(12) United States Patent
Goulmy

(10) Patent No.: US 6,830,883 B1
(45) Date of Patent: Dec. 14, 2004

(54) METHOD FOR TYPING OF MINOR HISTOCOMPATIBILITY ANTIGEN HA-1

(75) Inventor: Elsa Afra Julia Maria Goulmy, Oegstgeest (NL)

(73) Assignee: Rijksuniversiteit Leiden (NL)

( * ) Notice: Subject to any disclaimer, the term of this patent is extended or adjusted under 35 U.S.C. 154(b) by 0 days.

(21) Appl. No.: 09/269,250

(22) PCT Filed: Jul. 23, 1998

(86) PCT No.: PCT/EP98/04928

§ 371 (c)(1), (2), (4) Date: May 21, 1999

(87) PCT Pub. No.: WO99/05313

PCT Pub. Date: Feb. 4, 1999

(30) Foreign Application Priority Data

Jul. 23, 1997 (EP) ............................................ 97202303
Jun. 2, 1998 (EP) ............................................ 98870125

(51) Int. Cl.$^7$ ........................... C12Q 1/68; C12P 19/34; C07H 21/04
(52) U.S. Cl. ......................... 435/6; 435/91.1; 435/91.2; 536/23.1; 536/24.3
(58) Field of Search ......................... 435/6, 91.1, 91.2; 536/23.1, 24.3

(56) References Cited

U.S. PATENT DOCUMENTS 5,567,583 A * 10/1996 Wang et al. ................... 435/6

OTHER PUBLICATIONS

Harvey et al: Journal of Biological Chemistry, 1971, vol. 246, pp 4523–4530.*

* cited by examiner

*Primary Examiner*—Jehanne Sitton
(74) *Attorney, Agent, or Firm*—Robert D. Katz; Cooper & Dunham LLP

(57) ABSTRACT

The present invention provides a method for typing of alleles of the Minor Histocompatibility Antigen HA-1 in a sample. The method comprises: a) contacting the genomic polynucleic acids in the sample with at least one pair of primers, whereby the 5$^1$- and/or the 3$^1$-primer of the at least one pair of primers specifically hybridize to target regions comprising polymorphic nucleotides in the alleles, and performing an amplification reaction; b) for each of the at least one pair of primers detecting whether or not in step a) an amplification product is formed; c) inferring from the result of step b) which HA-1 allele is present in the sample. The present invention also provides a method for genomic typing of alleles of the Minor Histocompatibility Antigen HA-1 in a sample. This method comprises: a) amplifying a fragment of the alleles, with the fragment comprising at least one polymorphic nucleotide, by use of at least one pair of primers specifically hybridizing to conserved target region comprising one or more polymorphic nucleotides in the allele; c) inferring from the result of step b) which HA-1 allele is present in the sample. In addition, the present invention provides primers and probes for use in the above-mentioned methods. Diagnostic kits enabling the methods are also provided.

18 Claims, 12 Drawing Sheets

Figure 1A:
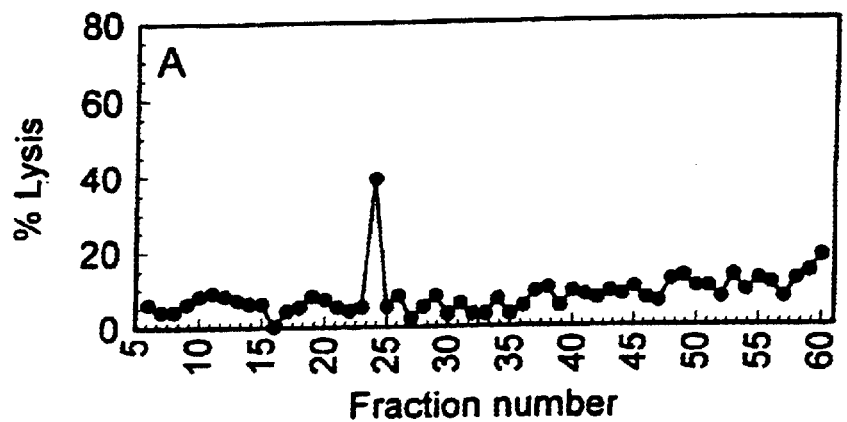

FIGURE 5A
FIGURE 5B
HA-1 specific CTL
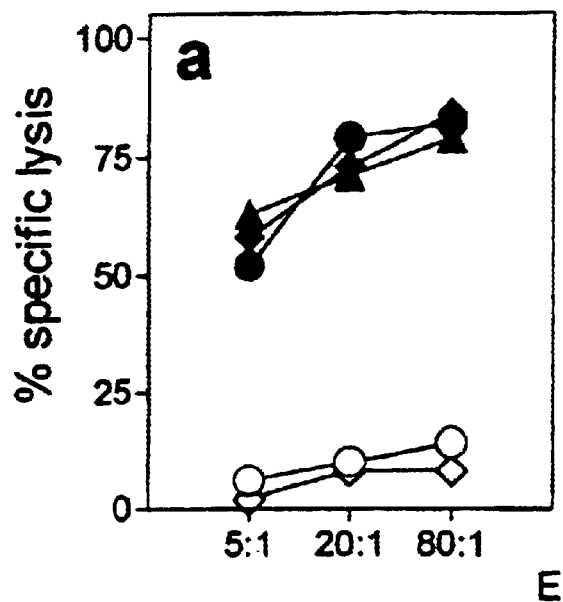
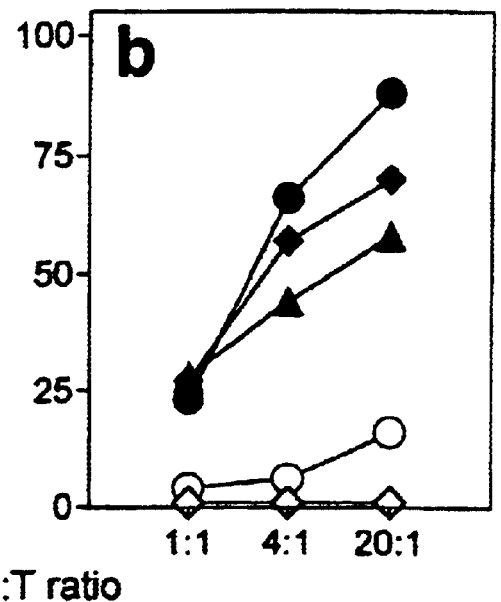
HA-2 specific CTL
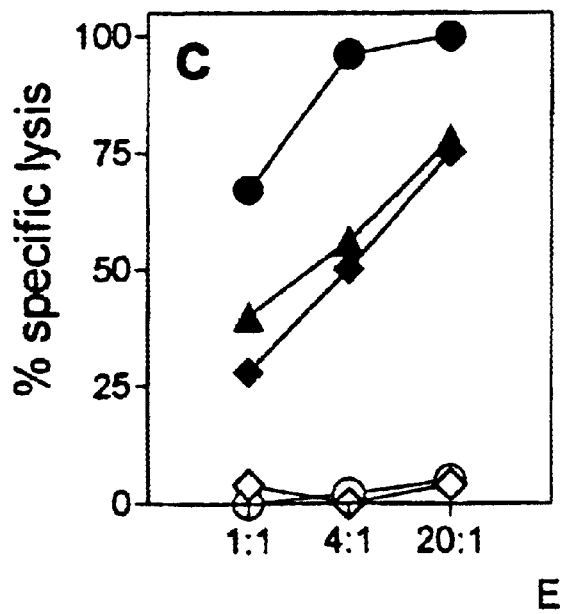
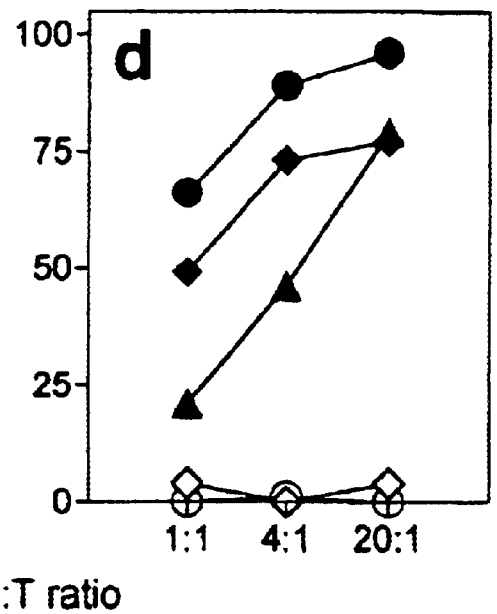
FIGURE 5C
FIGURE 5D FIGURE 6A
FIGURE 6B
HA-1 specific CTL
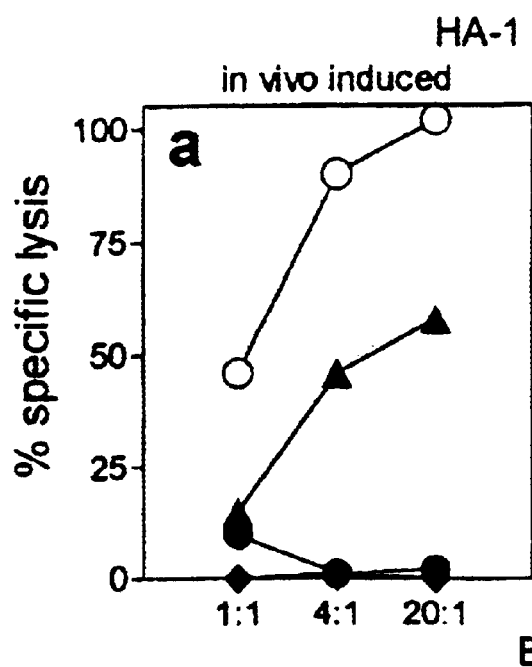
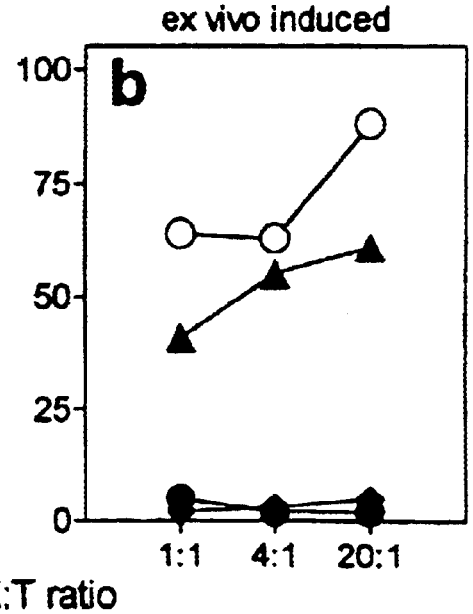
HA-2 specific CTL
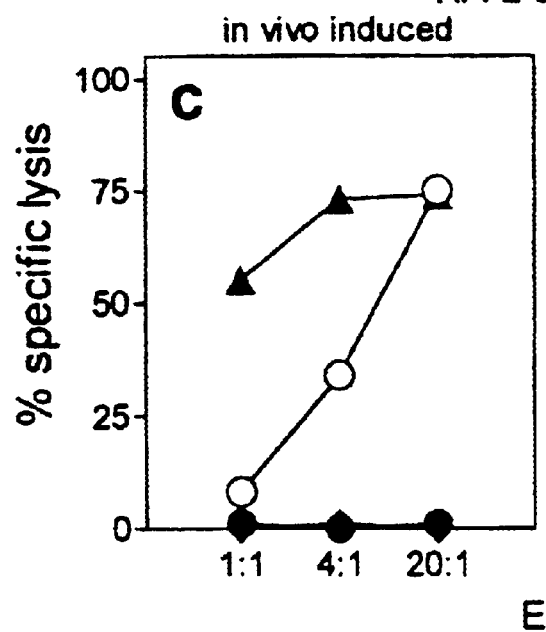
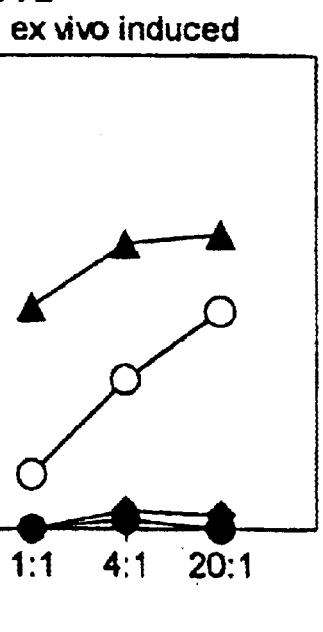
FIGURE 6C
FIGURE 6D FIGURE 7A
FIGURE 7B
FIGURE 7C
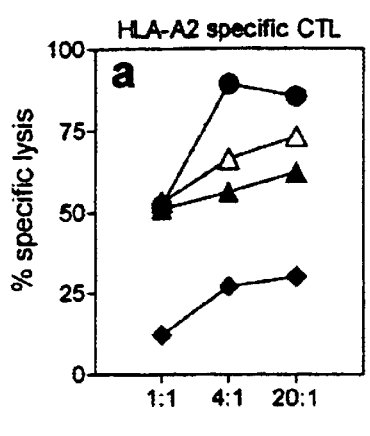
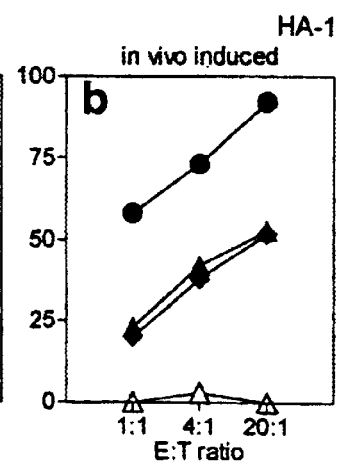
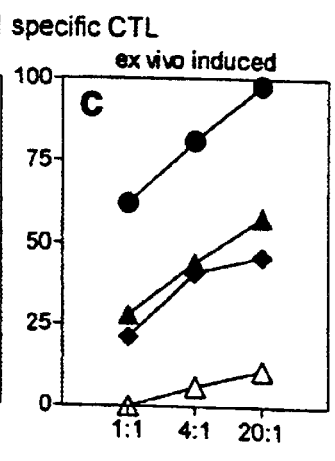
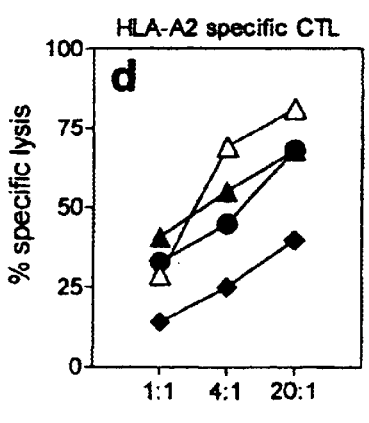
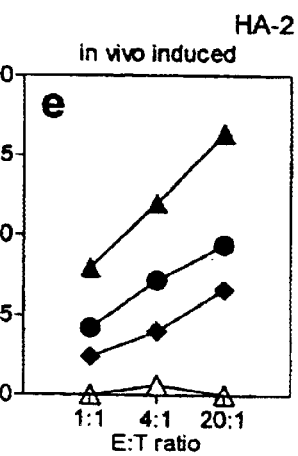
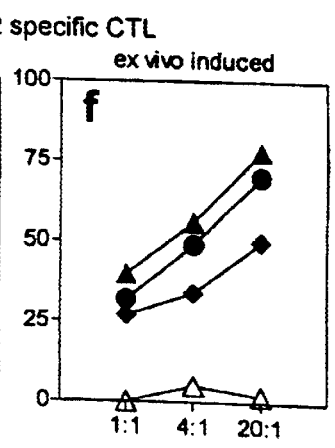
FIGURE 7D
FIGURE 7E
FIGURE 7F

SEQUENCE LISTING

<160> NUMBER OF SEQ ID NOS: 38

<210> SEQ ID NO 1
<211> LENGTH: 377
<212> TYPE: DNA
<213> ORGANISM: Human

<400> SEQUENCE: 1

| gtgagagcca cggggacacc gaggcctggg tggaagacag agccagaccc aagggaggat | 60 |
| gggagggaggg acttggggag gctcagaagg gagggaggct cagatggcag ggagggctgt | 120 |
| gtggaagagg ccatgacagc taaggctctg agggatgtgt aggagtttgg tgggggagtc | 180 |
| cctgagcgta cactggctca agagggtgcc cactttattt tttttaaagg atctgatggc | 240 |
| aattaggagg gaaaggcaga ggaaatgtcc catgcacagg ctcagaaaca cggaaacaga | 300 |
| gaatgcattt gggggccaag gtgtggggtg ccgctggtgt aggatgaagg catgacaacg | 360 |
| ccaggcagaa gggcaat | 377 |

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 2
gtgctgcctc ctggacactg                                         20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 3
tggctctcac cgtcatgcag                                         20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 4
tggctctcac cgtcacgcaa                                         20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 5
gcattctctg tttccgtgtt                                         20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 6
cttaaggagt gtgtgctgca                                         20

<210> SEQ ID NO 7
<211> LENGTH: 20

```
<212> TYPE: DNA
<213> ORGANISM: Artificial Sequence
<220> FEATURE:
<223> OTHER INFORMATION: Description of Artificial Sequence: Primer

<400> SEQUENCE: 7
cttaaggagt gtgtgttgcg                                               20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 8
gctgtcatgg cctcttccac                                               20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 9
gcattctctg tttccgtgtt                                               20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 10
ggcagagagc cctcgcagcc                                               20

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 11
gtgtgttgcg tgacggtg                                                 18

<210> SEQ ID NO 12
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 12
gtgtgttgcg tgacg                                                    15

<210> SEQ ID NO 13
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 13
```
tgtgtgttgc gtgacg                                                  16

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 14
tgtgtgctgc atgacggtg                                               19

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 15
tgtgtgctgc atgacggt                                                18

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 16
gtgtgctgca tgacggtg                                                18

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Exon
      Fragments
<220> FEATURE:
<221> NAME/KEY: CDS
<222> LOCATION: (1)..(27)
<223> OTHER INFORMATION:

<400> SEQUENCE: 17 gtg ttg cgt gac gac ctc ctt gag gcc                                27
Val Leu Arg Asp Asp Leu Leu Glu Ala
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Exon
      Fragments

<400> SEQUENCE: 18

Val Leu Arg Asp Asp Leu Leu Glu Ala
1               5

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Exon
      Fragments

```
<220> FEATURE:
<221> NAME/KEY: CDS
<222> LOCATION: (1)..(27)
<223> OTHER INFORMATION:

<400> SEQUENCE: 19 gtg ctg cat gac gac ctc ctt gag gcc                              27
Val Leu His Asp Asp Leu Leu Glu Ala
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Exon
      Fragments

<400> SEQUENCE: 20

Val Leu His Asp Asp Leu Leu Glu Ala
1               5

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Exon
      Fragments

<400> SEQUENCE: 21
gtgttgcgtg acggtgagag cca                                        23

<210> SEQ ID NO 22
<211> LENGTH: 37
<212> TYPE: DNA
<213> ORGANISM: Artificial Sequence
<220> FEATURE:
<223> OTHER INFORMATION: Description of Artificial Sequence: Exon
      Fragments

<400> SEQUENCE: 22
ctcactccga ctctccccag cagacctcct tgaggcc                         37

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 23
ccggcatgga cgtcgtcgag gacatctccc atc                             33

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 24
ctacttcagg ccacagcaat cgtctccagg                                 30

<210> SEQ ID NO 25
<211> LENGTH: 39
<212> TYPE: DNA
```

```
<213> ORGANISM: Artificial Sequence
<220> FEATURE:
<223> OTHER INFORMATION: Description of Artificial Sequence: PCR Product
<220> FEATURE:
<221> NAME/KEY: CDS
<222> LOCATION: (1)..(39)
<223> OTHER INFORMATION:

<400> SEQUENCE: 25 gag tgt gtg ttg cgt gac gac ctc ctt gag gcc cgc cgc          39
Glu Cys Val Leu Arg Asp Asp Leu Leu Glu Ala Arg Arg
1               5                   10

<210> SEQ ID NO 26
<211> LENGTH: 13
<212> TYPE: PRT
<213> ORGANISM: Artificial Sequence
<220> FEATURE:
<223> OTHER INFORMATION: Description of Artificial Sequence: PCR Product

<400> SEQUENCE: 26

Glu Cys Val Leu Arg Asp Asp Leu Leu Glu Ala Arg Arg
1               5                   10

<210> SEQ ID NO 27
<211> LENGTH: 39
<212> TYPE: DNA
<213> ORGANISM: Artificial Sequence
<220> FEATURE:
<223> OTHER INFORMATION: Description of Artificial Sequence: PCR Product
<220> FEATURE:
<221> NAME/KEY: CDS
<222> LOCATION: (1)..(39)
<223> OTHER INFORMATION:

<400> SEQUENCE: 27 gag tgt gtg ctg cat gac gac ctc ctt gag gcc cgc cgc          39
Glu Cys Val Leu His Asp Asp Leu Leu Glu Ala Arg Arg
1               5                   10

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence: PCR Product

<400> SEQUENCE: 28

Glu Cys Val Leu His Asp Asp Leu Leu Glu Ala Arg Arg
1               5                   10

<210> SEQ ID NO 29
<211> LENGTH: 9
<212> TYPE: PRT
<213> ORGANISM: Human
<220> FEATURE:
<221> NAME/KEY: MISC_FEATURE
<222> LOCATION: (3)..(3)
<223> OTHER INFORMATION: Xaa represents a histidine (H) or an arginine
      (R) residue

<400> SEQUENCE: 29

Val Leu Xaa Asp Asp Leu Leu Glu Ala
1               5

<210> SEQ ID NO 30
<211> LENGTH: 25
<212> TYPE: DNA
<213> ORGANISM: Artificial Sequence
```

<220> FEATURE:
<223> OTHER INFORMATION: Description of Artificial Sequence: Primer

<400> SEQUENCE: 30
gctcctgcat gacgctctgt ctgca    25

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 31
gacgtcgtcg aggacatctc ccat    24

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 32
gaaggccaca gcaatcgtct ccagg    25

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 33
ccttgagaaa cttaaggagt gtgtgctgca    30

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 34
ccttgagaaa cttaaggagt gtgtgttgcg    30

<210> SEQ ID NO 35
<211> LENGTH: 78
<212> TYPE: DNA
<213> ORGANISM: Artificial Sequence
<220> FEATURE:
<223> OTHER INFORMATION: Description of Artificial Sequence: PCR Product
<220> FEATURE:
<221> NAME/KEY: CDS
<222> LOCATION: (1)..(78)
<223> OTHER INFORMATION:

<400> SEQUENCE: 35 gag tgt gtg ttg cgt gac gac ctc ctt gag gcc cgc cgc gag tgt gtg    48
Glu Cys Val Leu Arg Asp Asp Leu Leu Glu Ala Arg Arg Glu Cys Val
1               5                   10                  15 ctg cat gac gac ctc ctt gag gcc cgc cgc                              78
Leu His Asp Asp Leu Leu Glu Ala Arg Arg
            20                  25

<210> SEQ ID NO 36

-continued

```
<211> LENGTH: 26
<212> TYPE: PRT
<213> ORGANISM: Artificial Sequence
<220> FEATURE:
<223> OTHER INFORMATION: Description of Artificial Sequence: PCR Product

<400> SEQUENCE: 36

Glu Cys Val Leu Arg Asp Asp Leu Leu Glu Ala Arg Arg Glu Cys Val
1               5                   10                  15

Leu His Asp Asp Leu Leu Glu Ala Arg Arg
            20                  25

<210> SEQ ID NO 37
<211> LENGTH: 9
<212> TYPE: PRT
<213> ORGANISM: Human
<220> FEATURE:
<221> NAME/KEY: MISC_FEATURE
<222> LOCATION: (2)..(2)
<223> OTHER INFORMATION: Xaa represents Isoleucine or Leucine

<400> SEQUENCE: 37

Tyr Xaa Thr Asp Arg Val Met Thr Val
1               5

<210> SEQ ID NO 38
<211> LENGTH: 8
<212> TYPE: PRT
<213> ORGANISM: HUMAN

<400> SEQUENCE: 38

Val Leu His Asp Leu Leu Glu Ala
1               5
```

METHOD FOR TYPING OF MINOR HISTOCOMPATIBILITY ANTIGEN HA-1

The present invention relates to the field of Minor Histocompatibility Antigen typing. Bone marrow transplantation (BMT), one of the areas the invention is concerned with and the area from which the present invention originates, finds its application in the treatment of for instance severe aplastic anaemia, leukaemia and immune deficiency diseases.

In the early days of this technique may transplants failed through rejection of the graft by the host. Transplants that did succeed, however often led to an immune response by lymphocytes present in the graft against various tissues of the host (Graft versus Host Disease (GvHD)). It is now known that the GvHD response is mainly due to the presence of major histocompatibility (H) antigens which present a transplantation barrier. Therefore it is now routine practice to graft only HLA-matched materials (either from siblings or unrelated individuals) resulting in a much improved rate of success in bone marrow transplantation. However, despite this improvement, as well as improvements in pre-transplantation chemotherapy or radiotherapy and the availability of potent immunosuppressive drugs, about 20–70% of the treated patients still suffer from GvHD (the percentage is age and bone marrow donor dependent). To avoid GvHD it has been suggested to remove the cells (mature T cells) causing said reaction from the graft. This however often leads to graft failure or to recurrence of the original diseases. The cells responsible for GvHD are also the cells which often react against the original aberrant cells in for insurance leukaemia (Graft versus Leukaemia response).

Since BMT is nowadays mainly carried out with HLA matched grafts, the GvHD which still occurs must be caused by another group of antigens. It is very likely that the group of so called minor H antigens (mHag), which are non-MHC encoded histocompatibility antigens (unlike the major H antigens) are at least partially responsible for the remaining incidence of GvHD. mHag's have originally been discovered in congeneic strains of mice in tumor rejection and skin rejection studies. In mice, the use of inbred strains has shown that mHag are encoded by almost 50 different allelically polymorphic loci scattered throughout the genome. In humans, although cumbersome to identify, mHag have been shown to exist, but their overall number and complexity remains uncertain. Minor H antigens are most likely quite different from each other and quite different from major H antigens, they are probably a diverse and elusive group of fragments of molecules which are participating in various cellular housekeeping functions. Their antigenicity may come very incidentally, as naturally processed fragments of polymorphic proteins that associate with MHC products. Some of the mH antigens appear to be widely expressed on various tissues throughout the body whereas other show limited tissue distribution.

One of the better known minor histocompatibility antigens in the H-Y antigen. H-Y is an mH antigen that can lead to rejection of HLA-matched male organ and bone marrow grafts by female recipients, and to a higher incidence of GvHD in female-to-male grafts, particularly if the female donor had been previously pregnant. The H-Y antigen may also play a role in spermatogenesis. The human H-Y antigen in an 11 residue peptide derived from SMCY, an evolutionary conserved Y chromosomal protein. Another well known mH antigen that can lead to GvHD is the HA-2 antigen. The human HA-2 antigen is an 9 residue peptide likely derived from a class 1 myosin. However, the nature of the HA-1 antigen, responsible for a majority of current cases of GvHD has remained elusive sofar. Human bone marrow transplants performed as therapeutical treatment of severe aplastic anemia, leukaemia and immune deficiency disease became available in the seventies. For the present, the long-term results of allogeneic bone marrow transplantation (BMT) have greatly improved due to the use of HLA-matched siblings as marrow donors, advanced pretransplant chemoradiotherapy, the use of potent immunsuppressive drugs as Graft-versus-Host-Disease (GVD) prophylaxis, better antibiotics and isolation procedures. Nonetheless, the results of clinical BMT reveal that the selection of MHC identical donors/recipients is not a guarantee of avoidance of GVHD or disease free survival even when donor and recipient are closely related. Allogeneic BMT especially in adults results, depending on the amount of T cell depletion of the graft, in uptil 80% of the cases in GVHD. In the HLA genotypically identical situation it amounts to 15–35% whereas in the phenotypical HLA matched recipient/donor combinations, the occurrence of GVHD is significantly higher i.e. 50–80%. Disparities for minor Histocompatibility antigens (mHag) between donor and recipient constitute a potential risk for GVHD or graft failure, which necessitate life long pharmacologic immunosuppression of organ and bone marrow transplant recipients. It is also believed that mHag are involved in the "beneficial" side effect of GVHD, i.e. the Graft-versus-Leukemia activity. Several reports demonstrated the presence of anti-host mHag specific CTL in patients suffering from GVHD after HLA genotypically identical BMT. In our laboratory, much effort was put into the further characterization of a (small) number of anti-host mHag specific CTLS. Hereto, CTL clones specific for host mHag were isolated from the peripheral blood (PBL) of patients suffering from severe GvHD. mHag HA-1 specific $CD8^+$ CTL clones were originally obtained after restimulation of in vivo primed PBLs from three patients suffering from GvHD after HLA identical but mHag nonidentical BMT. The post BMT CTL lines were cloned by limiting dilution, resulting in the isolation of a large number of mHag-specific CTL clones. Subsequent immunogeneic analyses revealed that the CTL clones (as described above) identified five non-sexlinked mHag, designated HA-1, -2, -3, -4, -5, which are recognized in an classical MHC restricted fashion. mHag HA-3 is recognized in the presence of HLA-A1 and mHag HA-1, -2, -4 and 5 require the presence of HLA-A2. Segregation studies demonstrated that each of mHag HA-1 to HA-5 is the product of a single gene segregating in a Menedelian fashion and that HA-1 and HA-2 are not coded within the HLA region. The mHag differ from each other in phenotype frequencies: mHag HA-1 appeared relatively frequent (i.e. 69%) whereas mHag HA-2 appeared very frequent (i.e. 95%) in the HLA-A2 positive healthy population. An inventory in five patients of mHag HA-1, -2, -3, -4 and -5 specific anti-host CTL response after BMT demonstrated in 3 patients clones specific for the mHag HA-1. This observation points towards the immunodominant behaviour of mhag HA-1. With regard to the mHag expressed on different tissues, we observed ubiquitous versus restricted tissue distribution of the mHag analysed. The expression of the mHag HA-1 is restricted to the cells of the haematopoietic cell lineage, such as thymocytes, peripheral blood lymphocytes, B cells, monocytes. Also the bone marrow derived professional antigen presenting cells: the dendritic cells and the epidermal Langerhans calls express the mHag HA-1. The mHag HA-1 is also expressed on clonogenic leukemic precursor cells as well as on freshly isolated myeloid and lymphoid leukemic cells, indicating that mHag specific CTLs are capable of HLA class I restricted antigen specific lysis of leukemic cells. To substantiate the importance of the human mH antigenic systems, we investigated whether the mHag are conserved in evolution between human and non human primates. Hereto, cells from non human primates were transfected with the human HLAA2.1 gene. Subsequent analyses with our human allo HLA-A2.1 and four mhag A2.1 restricted CTL clones revealed the presentation of ape and monkey allo and mHag HY. HA-1 and HA-2 peptides in the context of the transfected human HLA-A2.1 molecule by ape and monkey target cells. This implicates that the HA-1 peptide is conserved for at least 35 million years. A prospective study was performed in order to document the effect and clinical relevance of mHag in HLA genotypically identical BMT on the occurrence of acute (grade≧2) GVHD. The results of the mHag typing using the CTL clones specific for five well defined mHag HA-1 to HA-5 demonstrated a significant correlation between mHag HA-1, -2, -4 and -5 mismatch and GVHD. A significant correlation (P=0.024) with the development of GVHD was observed when analysed for only mHag HA-1. To anlayse a putative peptide nature of the mHag HA-1, we analysed the requirement of the MHC encoded TAP1 and TAP2 gene products for mhag peptide presentation on the cell surface. The transporter genes TAP1 and TAP2 associated with antigen presentation are required for delivery of peptides from the cytosol with the endoplasmic reticulum. The availability of a human celline "T2" lacking both transport and proteasome subunit genes enabled us to study the processing and presentation of human mHag. We demonstrated that the (rat) transport gene products TAP1 and TAP2u were required for processing and presentation of antigenic peptides from the intracellular mH protein HA-1. Information on the TCR repertoire post BMT in man is extremely scarce. We have anlaysed the composition of the T cell receptor (TCR) V region of mHag HA-1 specific CD8+ CTL clones of DNA sequencing of the α and β chains. We observed by analyzing TCR usage of 12 clones derived from 3 unrelated individuals that the TcRβ chains all used the TCRβV6S9 gene segment and showed remarkable similarities within the N-D-N regions.

However, until the present invention no one has succeeded in identifying amino acid sequences of antigenic peptides relevant to the mHag HA-1 antigen, nor has anyone succeeded in the identification of the proteins from which this antigen is derived.

It is therefore an aim of the present invention to derive the amino acid sequence of the HA-1 antigen.

It is also an aim of the present invention to derive the nucleic acid sequence of the HA-1 antigen, more particularly the cDNA and the genomic sequences encoding HA-1 antigens.

It is also an aim of the present invention to provide primers and probes enabling typing of HA-1 antigens.

It is also an aim of the present invention to provide kits allowing to type HA-1 antigens.

The present inventors have now for the first time identified a peptide which is a relevant part of mHag HA-1. The present inventors have also identified the cDNA sequence as well as the genomic sequence of two HA-1 alleles.

The present inventors describe for the first time a (poly) peptide comprising a T-cell epitope obtainable from the minor Histocompatibility antigen HA-1 comprising the sequence VLXDDLLEA (SEQ ID NO: 17) or a derivative thereof having similar functional or immunological properties, wherein X represents a histidine (H) or an arginine (R) residue.

Diagnostic applications envisaged in this invention include, but are not limited to HA-1 typing, detection of genetic aberrances and the like.

On the basis of the peptide described herein genetic probes or primers were produced which can be used to screen for the gene encoding the protein. On the basis of the peptide described herein anti-idiotypic B cells and/or T cells and antibodies can be produced. Various techniques, to allow detection of suitable donors or recipients, may be used, based on amplification of HA-1 related nucleic acid sequences or on the immunological detection of HA-1 related peptide sequences as set out further.

According to one embodiment, the present invention relates to a method for typing of alleles of the Minor Histocompatibility Antigen HA-1 in a sample comprising the detection of polymorphive nucleotides is the cDNA or genomic nucleic acids of said alleles, more particularly the H and R alleles of HA-1 as set out in FIG. 5.

In a preferred embodiment said method of typing will be a method of genomic DNA typing. Alternatively said method may also be a method of cDNA typing.

Another embodiment of the present invention relates to genomic typing of alleles of the Minor Histocompatibility Antigen HA-1 in a sample, with said method comprising:
  a) contacting the genomic polynucleic acids in the sample with at least one pair of primers, whereby the 5'- and/or the 3'-primer of said at least one pair of primers specifically hybridize to target regions comprising polymorphic nucleotides in said alleles, and performing an amplification reaction;
  b) for each of said at least one pair of primers detecting whether or not in step a) an amplification product is formed;
  c) inferring from the result of step b) which HA-1 allele is present in said sample.

According to a preferred embodiment, the present invention relates to a method as described above, further characterized in that said alleles of the Minor Histocompatibility Antigen HA-1 are the H allele and the R allele as shown in FIG. 5.

The present invention teaches that, unexpectedly, the primers used in the RT-PCR method, do not lead to amplification of a specific polynucleic acid fragment when genomic DNA is used as a template. To solve this problem, the present invention also discloses the genomic structure of the HA-1 locus. As explained in Example 3, analysis of the genomic structure shows that the HA-1 peptide is encoded by two exons (FIG. 5). A splice donor site is located four nucleotides after the polymorphic codon in the HA-1 coding sequence. Therefore, setting up a method for genomic typing of the HA-1 antigen requires sequence information of the intron interrupting the HA-1 codon sequence. This sequence information is provided by the present invention and is shown below as SEQ ID NO 1.

gtg aga gcc acg ggg aca ccg agg cct ggg tgg aag aca gag cca gac cca agg gag gat gga ggg agg gac ttg ggg agg ctc aga agg gag gga ggc tca gat ggc agg gag ggc tgt gtg gaa gag gcc atg aca gct aag gct ctg agg gat gtg tag gag ttt ggt ggg gga gtc cct gag cgt aca ctg gct caa gag ggt gco cac ttt att ttt rtt aaa gga tct gtt ggc aat tag gag gga aag gca gag gat atg tcc cat gca cag gct cag aaa cac gaa aac aga gac tgc att tgg ggg cca agg tgt ggg gtg ccg ctg gtg tag gat gan ggc atg aca acg cca ggc aga agg goa at SEQ ID NO 1

This sequence represents part of the interrupting intron (indicated as intron a in FIG. 5), the first nucleotide of this sequence being the first nucleotide of intron a. The present invention thus also relates to an isolated polynucleic acid identified by SEQ ID NO 1, or an isolated polynucleic acid displaying at least 80%, or at least 90%, or at least 95%, or at least 99% sequence homology to SEQ ID NO 1, or any fragment of said polynucleic acids that can be used as a primer or as a probe.

Sequence information corresponding to another part of intron a, more particularly the part which is situated in front of exon b (FIG. 5) has been dissolved in the EMBL database under accession number AC004151. However, this sequence is not suitable for the design of primers for the above-mentioned method, since the length of the amplified fragment would lower the efficiency of the amplification reaction.

The present invention also relates to isolated polynucleic acid identified by SEQ ID NO 17 (HA-1 R allele), or an isolated polynucleic acid displaying at least 80%, or at least 90%, or at least 95%, or at least 99% sequence homology to SEQ ID NO 17, or any fragment of said polynucleic acid that can be used as a primer or as a probe.

The present invention also relates to isolated polynucleic acid identified by SEQ ID NO 18 (HA-1 R allele), or an isolated polynucleic acid displaying at least 80%, or at least 90%, or at least 95%, or at least 99% sequence homology to SEQ ID NO 18, or any fragment of said polynucleic acid that can be used as a primer or as a probe.

The present invention also relates to any part of the sequence of KIAA0223 (GENBANK Acc. No. D 86976) which lies on the borders of SEQ ID NO 17 or 18, particularly sequence lying on the 5' side of SEQ ID NO 17 or 18 in the KIA0223 sequence. Such sequences are useful for the design of primers for HA-1 typing as disclosed in the present claims.

For detection of the amplification product mentioned in step b above, different methods known in the art, may be used. One method consists of subjecting the mixture obtained after the amplification reaction to gel electrophoresis and visually detecting the amplification product after nucleic staining. Alternatively, the amplification product may be labeled, for instance by using labeled primers, and may be captured on a solid support, for instance by hybridization, and may be detected on the solid support. It is clear, however, that other detection methods are also within the scope of the present invention.

According to a more preferred embodiment, the present invention relates to a method as indicated above, further characterized in that:

said at least one pair of primers comprise a 5'-primer that specifically hybridizes to a target region comprising the nucleotides at position 4 or at positions 4 and 8 in the HA-1 allele, or said at least one pair of primers comprises a 3'-primer that specifically hybridizes to a target region comprising the nucleotides at position 8 or at positions 4 and 8 in the HA-1 allele, with said positions being indicated in FIG. 5.

According to an even more preferred embodiment, the present invention relates to a method as indicated above, further characterized in that:

said 5'-primer is combined with a 3'-primer specifically hybridizing to a target region in introl a, and/or said 3'-primer is combined with a 5'-primer specifically hybridizing to a target region in exon a, with intron a and exon a being indicated in FIG. 5.

According to this embodiment, said target region in intron a is ideally located in the sequence identified by SEQ ID NO 1, as explained above. Also the target region of said 3'-primer that is combined with a 5'-primer specifically hybridizing to a target region in exon a, will necessarily overlap with the sequence identified by SEQ ID NO 1.

According to an even more preferred embodiment, the present invention relates to a method as indicated above, further characterized in that the primers are chosen from Table 1:

TABLE 1

Sequence of the primers used for genomic typing of HA-1 alleles by sequence-specific amplification.

| Name | Sequence (5' to 3') | SEQ ID NO |
| --- | --- | --- |
| Set 1 | | |
| C-forward | GTGCTGCCTCCTGGACACTG | 2 |
| H-reverse | TGGCTCTCACCGTCATGCAG | 3 |
| R-reverse | TGGCTCTCACCGTCACGCAA | 4 |
| Set 2 | | |
| C-reverse | GCATTCTCTGTTTCCGTGTT | 5 |
| H-forward | CTTAAGGAGTGTGTGCTGCA | 6 |
| R-forward | CTTAAGGAGTGTGTGTTGCG | 7 |

Set 1 consists of a common 5'-primer (forward) and two different 3'-primers (reverse), one for the H allele and one for the R allele. The target region of the common 5'-primer is located in exon a. The target region of the 3'-position comprises the polymorphic nucleotides at positions 4 and 8 in the HA-1 coding sequence (FIG. 5) and partly overlaps with the sequence identified by SEQ ID NO 1. Set 2 consists of a common 3'-primer and two different 5'-primers. The target region of the common primer is located in the sequence identified by SEQ ID NO 1, whereas the target regions of the 5'-primers are located in exon a and comprise the polymorphic nucleotides at position 4 and 8. Example 6 shows a genomic type experiment making use of these primer sets.

According to another preferred embodiment, the present invention relates to a diagnostic kit for genomic typing of alleles of the Minor Histocompatibility Antigen HA-1 according to any of the methods indicated above, with said kit comprising:

a) at least one primer according to any of the methods indicated above;

b) optionally, an enzyme and/or reagent enabling the amplification reaction;

c) optionally, means enabling direction of the amplified products.

According to another preferred embodiment, the present invention relates to a method for genomic typing of alleles of the Minor Histocompatibility Antigen HA-1 in a sample, with said method comprising:

a) amplifying a fragment of said alleles, with said fragment comprising at least one polymorphic nucleotide, by use of at least one pair of primers specifically hybridizing to conserved target regions in said alleles;

b) hybridizing the amplified product of step a) to at least one probe specifically hybridizing to a target region comprising one or more polymorphic nucleotides in said allele;

c) inferring from the result of step b) which HA-1 allele is present in said sample.

According to a more preferred embodiment, the present invention relates to a method as indicated above, further characterized in that said alleles of the Minor Histocompatibility Antigen HA-1 are the H allele and the R allele.

According to an even more preferred embodiment, the present invention relates to a method as indicated above, further characterized in that said at least one pair of primers comprises 5'-primer specifically hybridizing to a conserved target region in exon a and/or a 3'-primer specifically hybridizing to a conserved target region in intron a, with exon and intron a being indicated in FIG. 5.

Ideally, the target region of said 3'-primer is located in the sequence identified as SEQ ID NO 1. Obviously, the target region of said 3'-primer may also be located downstream of this sequence, i.e. in intron a, intron b, exon b, or even downstream of exon b, but the efficacy of the amplification reaction is likely to be lower as the amplified fragment becomes longer. According to an even more preferred embodiment, the present invention relates to a method as indicated above, further characterized in that said at least one probe specifically hybridizes to a target region comprising the nucleotides at position 4 and/or 8 in the HA-1 allele, with said positions being indicated in FIG. 5.

According to an even more preferred embodiment, the present invention relates to a method as indicated above, further characterized in that said primers and/or said probes are chosen from Table 2:

TABLE 2

Sequence of the primers and probes used for genomic typing of HA-1 alleles by amplification and sequence-specific hybridization

| Name | Sequence (5' to 3') | SEQ ID NO |
|---|---|---|
| Primers | | |
| 5P1 (= C-forward) | GTGCTGCCTCCTGGACACTG | 2 |
| 3P1 | GCTGTCATGGCCTCTTCCAC | 8 |
| 3P2 | GCATTCTCTGTTTCCGTGTT | 9 |
| 3P3 | GGCAGAGAGCCCTCGCAGCC | 10 |
| Probes | | |
| HA1-R1(1) | GTGTGTTGCGTGACGGTG | 11 |
| HA1-R1(2) | GTGTGTTGCGTGACG | 12 |
| HA1-R1(3) | TGTGTGTTGCGTGACG | 13 |
| HA1-H1(1) | TGTGTGCTGCATGACGGTG | 14 |
| HA1-H1(2) | TGTGTGCTGCATGACGGT | 15 |
| HA1-H1(3) | GTGTGCTGCATGACGGTG | 16 |

Primers 3P1 and 3P2 specifically hybridize target regions in SEQ ID NO 1. The target region of primer 3P3 is located downstream of exon b. The probes of Table 2 all specifically hybridize to target regions overlapping with the exon a-intron a boundary. The probes with SEQ ID NO 11 to 16 have been optimized to function in combination at the same conditions in a LiPA assay (see below). The skilled man will recognize that the probes and primers with SEQ ID NO 2 to 16 may be adapted by addition or deletion of one or more nucleotides at their extremities. Such adaptations may be required if the conditions of amplification or hybridization are changed, or if the amplified material is RNA instead of DNA, as in the case in the NASBA system. Different techniques can be applied to perform the sequence-specific hybridization methods of the present invention. These techniques may comprise immobilizing the amplified HA-1 polynucleic acids on a solid support and performing hybridization with labelled oligonucleotide probes. Genomic polynucleic acids may also be immobilized on a solid support without prior amplification and subjected to hybridization. Alternatively, the probes may be immobilized on a solid support and hybridization may be performed with labelled HA-1 polynucleic acids, preferably after amplification. This technique is called reverse hybridization. A convenient reverse hybridization technique is the line probe assay (LiPA). This assay uses oligonucleotide probes immobilized as parallel lines on a solid support strip (Stuyver et al., 1993). It is to be understood that any other technique for genomic typing of HA-1 alleles is also conveyed by the present invention.

It is clear that the present invention also relates to any of the primers with SEQ ID NO 2 to 10 and to any of the probes with SEQ ID NO 11 to 16, with said primers and said probes being for use in a method for genomic typing of alleles of the Minor Histocompatibility Antigen HA-1.

According to another preferred embodiment, the present invention relates to a diagnostic kit for genomic typing of alleles of the Minor Histocompatibility Antigen HA-1 according to any of the sequence-specific hybridization methods indicated above, with said kit comprising:

a) at least one primer according to any of the methods indicated above;

b) optionally, an enzyme and/or reagents enabling the amplification reaction, and/or reagents enabling the hybridization reaction.

According to another preferred embodiment, the present invention relates to a diagnostic kit for genomic typing of alleles of the Minor Histocompatibility Antigen HA-1 according to any of the sequence-specific hybridization methods indicated above, with said kit comprising:

a) at least one primer according to any of the methods indicated above;

b) at least one probe according to any of the methods indicated above;

c) optionally, an enzyme and/or reagents enabling the amplification reaction, and/or reagents enabling the hybridization reaction.

According to another embodiment, the present invention also relates to a method for typing of alleles of the Minor Histocompatibility Antigen HA-1 by means of sequencing said allele.

According to another embodiment, the present invention also relates to kits for performing said sequencing method.

According to another embodiment, the present invention also relates to a method for typing HLA-1 alleles comprising using antibodies specifically detecting the HA-1 alleles shown in FIG. 5. Said antibodies will be preferably monoclonal antibodies and can be produced by any method shown in the art.

According to another embodiment, the present invention also relates to a diagnostic kit for typing HLA-1 allele comprising using antibodies specifically detecting the HA-1 alleles shown in FIG. 5.

DEFINITIONS

The following definitions and explanations will permit a better understanding of the present invention.

The target material in the samples to be anlaysed will be genomic DNA or amplified versions thereof. These molecules are in this application also termed "polynucleic acids". Well-known extraction and purification procedures are available for the isolation of RNA or DNA from a sample (e.g. in Sambrook et al., 1989).

A "polymorphic nucleotide" refers to a nucleotide of the sequence of a given HA-1 allele that differs from at least one of the nucleotides that are found at the corresponding position in other HA-1 alleles.

The term "typing" of an HA-1 allele refers to identification of the allele, i.e. detection of the allele and discrimination of the allele from other HA-1 alleles. The term "probe" according to the present invention refers to a single-stranded oligonucleotide which is designed to specifically hybridize to HA-1 polynucleic acids. Preferably, the probes of the invention are about 5 to 50 nucleotides long, more preferably from about 10 to 30 nucleotides. Particularly preferred lengths of probes include 10, 11, 12, 13, 14, 15, 16, 17, 18, 19, 20, 21, 22, 23, 24, 25, 26, 27, 28, 29 or 30 nucleotides. The nucleotides as used in the present invention may be ribonucleotides, deoxyribonucleotides and modified nucleotides such as inosine or nucleotides containing modified groups which do not essentially alter their hybridization characteristics.

The term "primer" refers to a single stranded oligonucleotide sequence capable of acting as a point of initiation for synthesis of a primer extension product which is complementary to the nucleic acid strand to be copied. The length and the sequence of the primer must be such that they allow to prime the synthesis of the extension products. Preferably the primer is about 5–50 nucleotides long. Specific length and sequence will depend on the complexity of the required DNA or RNA target, as well as on the conditions at which the primer is used, such as temperature and ionic strength. It is to be understood that the primers of the present invention may be used as probes and vice versa, provided that the experimental conditions are adapted.

The expression "suitable primer pair" in this invention refers to a pair of primers allowing specific amplification of a HA-1 polynucleic acid fragment. The term "target region" of a probe or a primer according to the present invention is a sequence within the HA-1 polynucleic acids to which the probe or the primer is completely complementary or partially complementary (i.e. with some degree of mismatch). It is to be understood that the complement of said target sequence is also a suitable target sequence in some cases.

"Specific hybridization" of a probe to a target region of the HA-1 polynucleic acids means that said probe forms a duplex with part of this region or with the entire region under the experimental conditions used, and that under those conditions said probe does not form a duplex with other regions of the polynucleic acids present in the sample to be anlaysed. "Specific hybridization" of a primer to a target region of the HA-1 polynucleic acids means that, during the amplification step, said primer forms a duplex with part of this region or with the entire region under the experimental conditions used, and that under those conditions said primer does not form a duplex with other regions of the polynucleic acids present in the sample to be analysed. It is to be understood that "duplex" as used hereby, means a duplex that will lead to specific amplification.

"Specific amplification" of a fragment of the HA-1 polynucleic acids means amplification of the fragment for which the primers were designed, and not of any other fragment of the polynucleic acids present in a sample.

The fact that amplification primers do not have to match exactly with the corresponding target sequence in the template to warrant proper amplification is amply documented in the literature (Kwok et al, 1990). However, when the primers are not completely complementary to their target sequence, it should be taken into account that the amplified fragments will have the sequence of the primers and not of the target sequence. Primers may be labelled with a label of choice (e.g. biotin). The amplification method used can be either polymerase chain reaction (PCR; Saiki et al., 1988), ligase chain reaction (LCR; Landgren et al., 1988; Wu & Wallace, 1989; Barany, 1991), nucleic acid sequence-based amplification (NASBA; Guatelli et al., 1990; Compton, 1991), transcription-based amplification system (TAS; Kwoh et al., 1989), strand displacement amplification (SDA; Dunk, 1990) or amplification by means of QB replicase (Lomeli et al., 1989) or any other suitable method to amplify nucleic acid molecules known in the art.

Probe and primer sequences are represented throughout the specification as single stranded DNA oligonucleotides from the 5' to the 3' end. It is obvious to the man skilled in the art that any of the below-specified probes can be used as such, or in their complementary form, or in their RNA form (wherein T is replaced by U).

The probes according to the invention can be prepared by cloning of recombinant plasmids containing inserts including the corresponding nucleotide sequence, if need be by excision of the latter from the cloned plasmids by use of the adequate nucleases and recovering them, e.g. by fractionation according to molecular weight. The probes according to the present invention can also be synthesized chemically, for instance by the conventional phospho-trietter method.

The oligonucleotides used as primers or probes may also comprise nucleotide analogues such as phosphorothiates (Matsukura et al., 1987), alkylphosphorothiates (Miller et al., 1979) or peptide nucleic acids (Nielsen et al., 1991; Nielsen et al., 1993) or may contain intercalating agents (Asseline et al., 1984). As most other variations or modifications introduced into the original DNA sequences of the invention these variations will necessitate adaptations with respect to the conditions under which the oligonucleotide should be used to obtain the required specificity and sensitivity. However the eventual results of hybridization will be essentially the same as those obtained with the unmodified oligonucleotides. The introduction of these modifications may be advantageous in order to positively influence characteristics such as hybridization kinetics, reversibility of the hybrid-formation, biological stability of the oligonucleotides molecules, etc.

The term "solid support" can refer to any substrate to which an oligonucleotide probe can be coupled, provided that it retains its hybridization characteristics and provided that the background level of hybridization remains low. Usually the solid substrate will be a microtiter plate, a membrane (e.g. nylon or nitrocellulose) or a microsphere (bead) or a chip. Prior to application to the membrane or fixation it may be convenient to modify the nucleic acid probe in order to facilitate fixation or improve the hybridization efficiency. Such modifications may encompass homopolymer tailing, coupling with different reactive groups such as aliphatic groups, $NH_2$ groups, SH groups, carboxylic groups, or coupling with biotin, haptens or proteins.

The term "labelled" refers to the use of labelled nucleic acids. Labelling may be carried out by the use of labelled nucleotides incorporated during the polymerase step of the amplification such as illustrated by Saiki et al. (1988) or Bej et al. (1990) or labelled primers, or by any other method known to the person skilled in the art. The nature of the label may be isotopic ($^{32}P$, $^{35}S$, etc.) or non-isotopic (biotin, digoxigenin, etc.).

The "biological sample" may be for instance blood, mouth swab or any other sample comprising genomic DNA.

For designing probes with desired characteristics, the following useful guidelines known to the person skilled in the art can be applied.

Because the extent and specificity of hybridization reactions such as those described herein are affected by a number of factors, manipulation of one or more of those factors will determine the exact sensitivity and specificity of a particular probe, whether perfectly complementary to its target or not. The importance and effect of various assay conditions are explained further herein.

The stability of the [probe:target] nucleic acid hybrid should be chosen to be compatible with the assay conditions. This may be accomplished by avoiding long AT-rich sequences, by terminating the hybrids with G:C base pairs, and by designing the probe with an appropriate Tm. The beginning and end points of the probe should be chosen so that the length and %GC result in a Tm about 2–10° C. higher than the temperature at which the final assay will be performed. The base composition of the probe is significance because G-C base pairs exhibit greater thermal stability as compared to A-T base pairs due to additional hydrogen bonding. Thus, hybridization involving complementary nucleic acids of higher G-C content will be more stable at higher temperatures.

Conditions such as inionic strength and incubation temperature under which a probe will be used should also be taken into account when designing a probe. It is known that the degree of hybridization will increase as the ionic strength of the reaction mixture increases, and that the thermal stability of the hybrids will increase with increasing ionic strength. On the other hand, chemical reagents, such as formamide, urea, DMSO and alcohols, which disrupt hydrogen bonds, will increase the stringency of hybridization. Destabilization of the hydrogen bonds or such reagents can greatly reduce the Tm. In general, optimal hybridization for synthetic oligonucleotide probes of about 10–50 bases in length occurs approximately 5° C. below the melting temperature for a given duplex. Incubation at temperatures below the optimum may allow mismatched base sequences to hybridize and can therefore result in reduced specificity.

It is desirable to have probes which hybridize only under conditions of high stringency. Under high stringency conditions only highly complementary nucleic acid hybrids will form; hybrids without a sufficient degree of complementarity will not form. Accordingly, the stringency of the assay conditions determines the amount of complementarity needed between two nucleic acid strands forming a hybrid. The degree of stringency is chosen such as to maximize the difference in stability between the hybrid formed with the target and the non-target nucleic acid.

Regions in the target DNA or RNA which are known to form strong internal structures inhibitory to hybridization are less preferred. Likewise, probes with extensive self-complementarity should be avoided. As explained above, hybridization is the association of two single strands of complementary nucleic acids to form a hydrogen bonded double strand. It is implicit that if one of the two strands is wholly or partially involved in a hybrid that it will be less able to participate in formation of a new hybrid. There can be intramolecular and intermolecular hybrids formed within the molecules of one type of probe if there is sufficient self complementarity. Such structures can be avoided through careful probe design. By designing a probe so that a substantial portion of the sequence of interest is single stranded, the rate and extent of hybridization may be greatly increased. Computer programs are available to search for this type of interrraction. However, in certain instances, it may not be possible to avoid this type of interaction.

Standard hybridization and wash conditions are disclosed in the Materials & Methods section of the Examples. Other conditions are for instance 3× SSC (Sodium Salt Citrate), 20% deionized FA (Formamide) at 50° C. Other solutions (SSPE (Sodium saline phosphate EDTA), TMAC (Tetramethyl ammonium Chloride), etc.) and temperatures can also be used provided that the specificity and sensitivity of the probes is maintained. When needed, slight modifications of the probes in length or in sequence have to be carried out to maintain the specificity and sensitivity required under the given circumstances.

The term "hybridization buffer" means a buffer allowing a hybridization reaction between the probes and the polynucleic acids present in the sample, or the amplified products, under the appropriate stringency conditions.

The term "wash solution" means a solution enabling washing of the hybrids formed under the appropriate stringency conditions.

BRIEF DESCRIPTION OF THE DRAWINGS AND TABLES

Table 1
Sequence of the primers used for genomic typing of HA-1 alleles by sequence-specific amplification.
Table 2
Sequence of the primers and probes used for genomic typing of HA-1 alleles by amplification and sequence-specific hybridization.
Table 3
Cellular and genomic typing for HA-1 in three HLA-A*0201 positive families
Table 4
Comparison of cellular and genomic typing by PCR or LiPA of HA-1 in family 1.
Table 5 (Sequence ID Nos.: 25–28)
KIAA0223 sequence polymorphism in mH HA-1 positive and HA-1 negative individuals. Sequencing of HA-1 region in KIAA0223 gene in HA-1+/+ and HA-1−/− homozygous individuals and KG-1 revealed two alleles differing in two nucleotides resulting in a one amino acid difference (H to R) and designated HA-1$^H$ and HA-1$^R$. For DH and vR 6 independent PCR products were sequenced. For KG-1 8 PCR products were sequenced.

FIG. 1. Reconstitution of HA-1 with HPLC fractionated peptides eluted from HLA-A2.1 molecules in a $^{51}$Cr-release assay with mH HA-1 specific T cell clone 3HA15.
 a. Peptides were eluted from 90.10$^9$ HA-1 and HA-A2.1 positive Rp cells and separated using reverse phase HPLC with HFBA as organic modifier.
 b. Fraction 24 of the first HPLC dimension that contained HA-1 activity was further fractionated by reverse phase HPLC with TFA as organic modifier.
 c. HA-1 containing fraction 27 of the second gradient was further chromatographed with a third shallower gradient consisting of 0.1% acetonitrile/min. Background lysis of T2 by the CTL in the absence of any peptides was in a 3%, in b and c, 0%. Positive control lysis was in a 99%, in b 74% and in c 66%.
 d: Determination of candidate HA-1 peptides. HPLC fraction 33 from the separation in FIG. 1c. was chromatographed with an on-line microcapillary column effluent splitter and anaysed by electrospray ionization mass spectrometry and a $^{51}$Cr-release assay. HA-1 reconstituting activity as percent specific release was compared with the abundance of peptide candidates measured as ion current.

FIG. 2. Sequencing of mH HA-1 peptide by tandem mass spectrometry.
 a. Collision activation dissociation mass spectrum of peptide candidate with m/z of 513.

b. Reconstitution assay with different concentrations of synthetic mH HA-1 peptide with three HA-1 specific T cell clones, 3HA15, clone 15 and 5W38. Background lysis of T2 by the CTL in the absence of any peptide was for 3HA15 4%, for clone 15 10% and for 5W38 2%. Positive control lysis was for 3HA15 46%, for clone 15 47% and 5W38 48 48%.

FIG. 3. KIAA0223 polymorphism exactly correlated with mH antigen HA-1 phenotype.

a. The HA-1 region of KIAA0223 was sequenced in a HA-1 mH antigen typed family. 6 PCR products of each family member were sequenced. Family members 00, 07 and 09 expressed the HA-1$^R$ in all 6 PCR products. Family members 01 expressed the HA-1$^H$ allele in 2 PCR products and the HA-1$^R$ allele in 4 PCR products. Family member 02 expressed the HA-1$^H$ allele in 3 PCR products and the HA-1$^R$ allele in 3 PCR products. Family member 08 expressed the HA-1$^H$ allele in 4 PCR products and the HA-1$^R$ allele in 2 PCR products.

b. HA-1 allele specific PCR reaction in a HA-1 mH antigen typed family correlated exactly with the HA-1 phenotype. The sizes of the resulting PCR products were consistent with the expected sizes deduced from the cDNA sequence.

c. Transfection of the HA-1$^H$ allele of KIAA0223 leads to recognition of mH HA-1 specific T cells. The HA-1$^H$ and the HA-1$^R$ coding sequence of KIAA0223 were together with HLA-A2.1 transfected into Hela cells. After 3 days the HA-1 specific CTL clones 5W38 and 3HA15 were added and after the 24 hours TNFα release was measured in the supernatant. The clone Q66.9 is specific for the influenza matrix peptide 58–66. No TNFα production was observed after transfection of the pcDNA3.1(+) vector alone (results not shown).

FIG. 4.

a. Binding of HA-1$^H$ and HA-1$^R$ peptides to HLA-A2.1. The binding of HA-1$^H$ and HA-1$^R$ peptides were assayed for their ability to inhibit the binding of fluorescent peptide FLPSDCFPSV to recombinant HLA-A2.1 and β2-microglobulin in a cell free peptide binding assay. One representative experiment is shown. The IC50 is determined on the results of 4 experiments and was 30 nM for VLHDDLLEA and 365 nM for VLRDDLLEA, b. Reconstitution assay with different concentrations of synthetic HLA-1$^R$ peptide with HA-1 specific T cells. The HA-1$^R$ peptide was titrated and preincubated with T2 cells. Three HA-1 specific T cells clones, 5W38, 3HA15 and clone 15 were added and a 4 hr $^{51}$Cr-release assay was performed. Background lysis of T2 by the CTL in the absence of any peptide was for 3HA15 4%, for clone 15 10% and for 5W38 2%. Positive control lysis was for 3HA15 46%, for clone 15 47% and 5W38 48%.

Figure 1B:
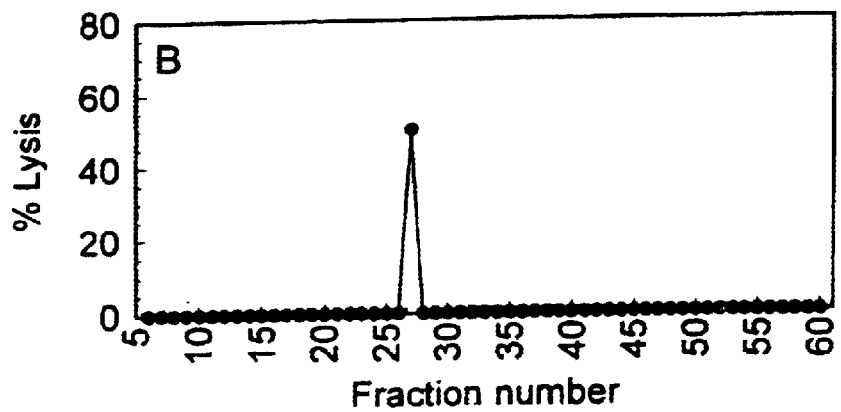
Figure 1C:
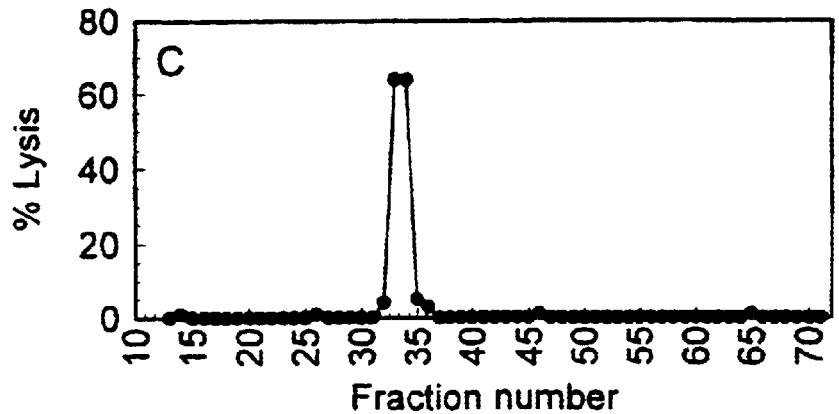

FIG. 5 (Sequence ID Nos.: 17–22) Sequences and genomic structure of the HA-1 locus. FIG. 1a, coding sequences of the H and R alleles of HA-1. Bold characters indicate the polymorphic nucleotides. FIG. 1b, exon-intron boundaries of the HA-1 locus. Exon sequences are shown in uppercase, intron sequences in lowercase.

FIG. 6 Genomic typing of HA-1 alleles in clinical samples. Genomic typing was performed by sequence-specific amplification, by use of the two primer sets of Table 1. The two upper fragments in the gel originate from the H-allele, the two lower fragments from the R-allele.

EXAMPLES

1. Examples 1 cDNA Preparation of HA-1

1.1 Results

Graft-versus-Host Disease (GvHD) is a frequent and life-threatening complication after allogeneic HLA-identical bone marrow transplantation (BMT). Recipients of HLA-identical bone marrow develop acute or chronic Graft-versus-Host-Disease in respectively 36% and 49%[1-2]. Disparities in genes other than the MHC, referred to as minor histocompatibility (mH) antigens, are clearly involved in the development of GvHD after HLA-identical BMT. A recent retrospective analysis revealed the significant association between mismatching for the mH antigen HA-1 and the induction of GvHD after HLA-identical BMT[3]. Minor histocompatibility antigens are recognized by MHC restricted T cells and were shown to be peptides derived from intracellular proteins presented by MHC molecules[4-6]. Here we report the first identification of a polymorphic gene encoding an human mH antigen. The GvHD associated mH antigen HA-1 is a nonapeptide derived from the di-allelic KIAA0223 gene. The HA-1 allelic counterpart encoded by the KIAA0223 gene differs only at one amino acid from the mH antigen HA-1. Family studies demonstrated an exact correlation between the KIAA0223 gene polymorphism and the HA-1 phenotype as was previously determined by recognition by the HA-1 specific CTL clones. The elucidation of the HA-1 encoding gene enables prospective HA-1 DNA typing of BMT donors and recipients to improve donor selection and prevention of GvHD.

Cytotoxic T cell clones specific for the mH antigen HA-1 have been isolated from three different patients with severe GvHD[7]. The mH antigen HA-1 is presented in the context of HLA-A2.1 and present in 69% of the HLA-A2.1 positive population[7]. HA-1 expression was demonstrated to be tissue specific and limited to cells of haematopoietic origin, including dendritic cells. Langerhans cells and leukemic cells[9,10]. Family analysis indicated a mendelian mode of inheritance for HA-1 and segregation independent from the MHC complex[11]. Comparison of the T cell receptor (TCR) sequences of different HA-1 specific T cell clones derived from different individuals revealed conserved usage of the TCR Vβ6.9 and conserved amino acids in the CDR3 region[12]. In a retrospective study, mismatching for a number of mH antigens was evaluated with regard to the association with GvHD after HLA-identical BMT. A single HA-1 mismatch between donor and recipient was significantly correlated with the induction of GvHD after HLA-identical BMT[3].

Figure 1D:
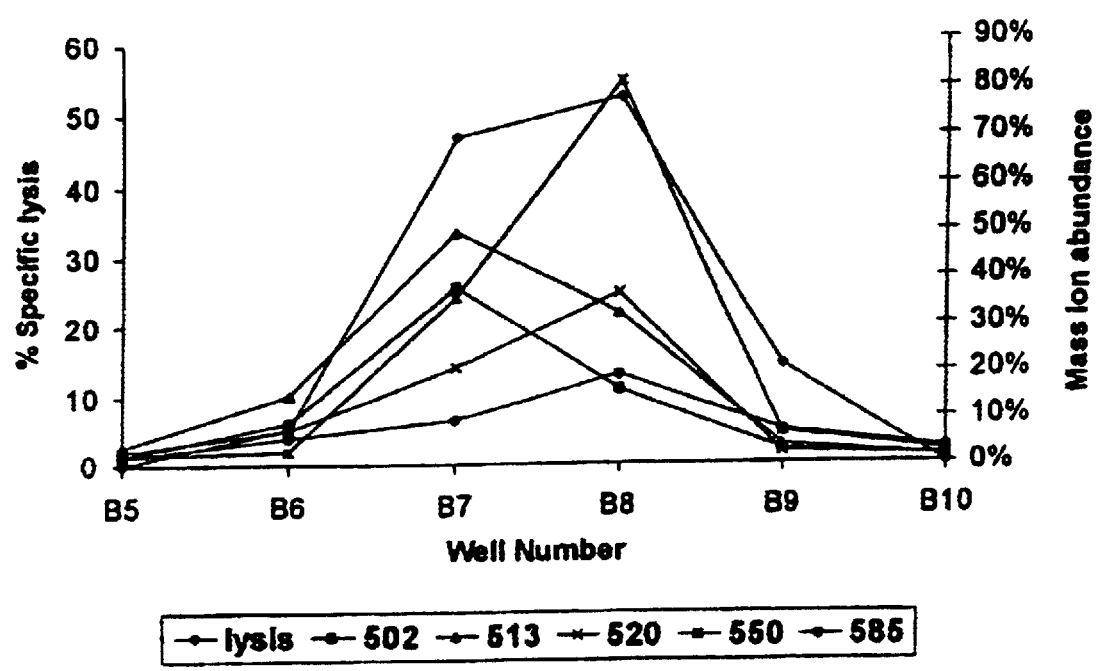
Figure 2A:
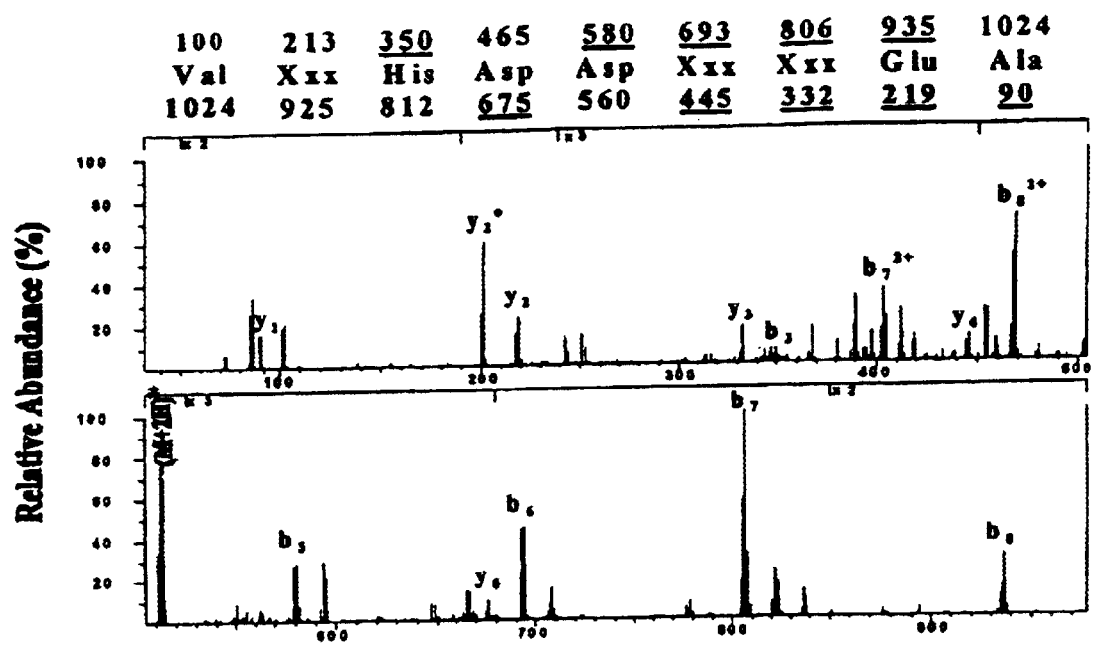
Figure 2B:
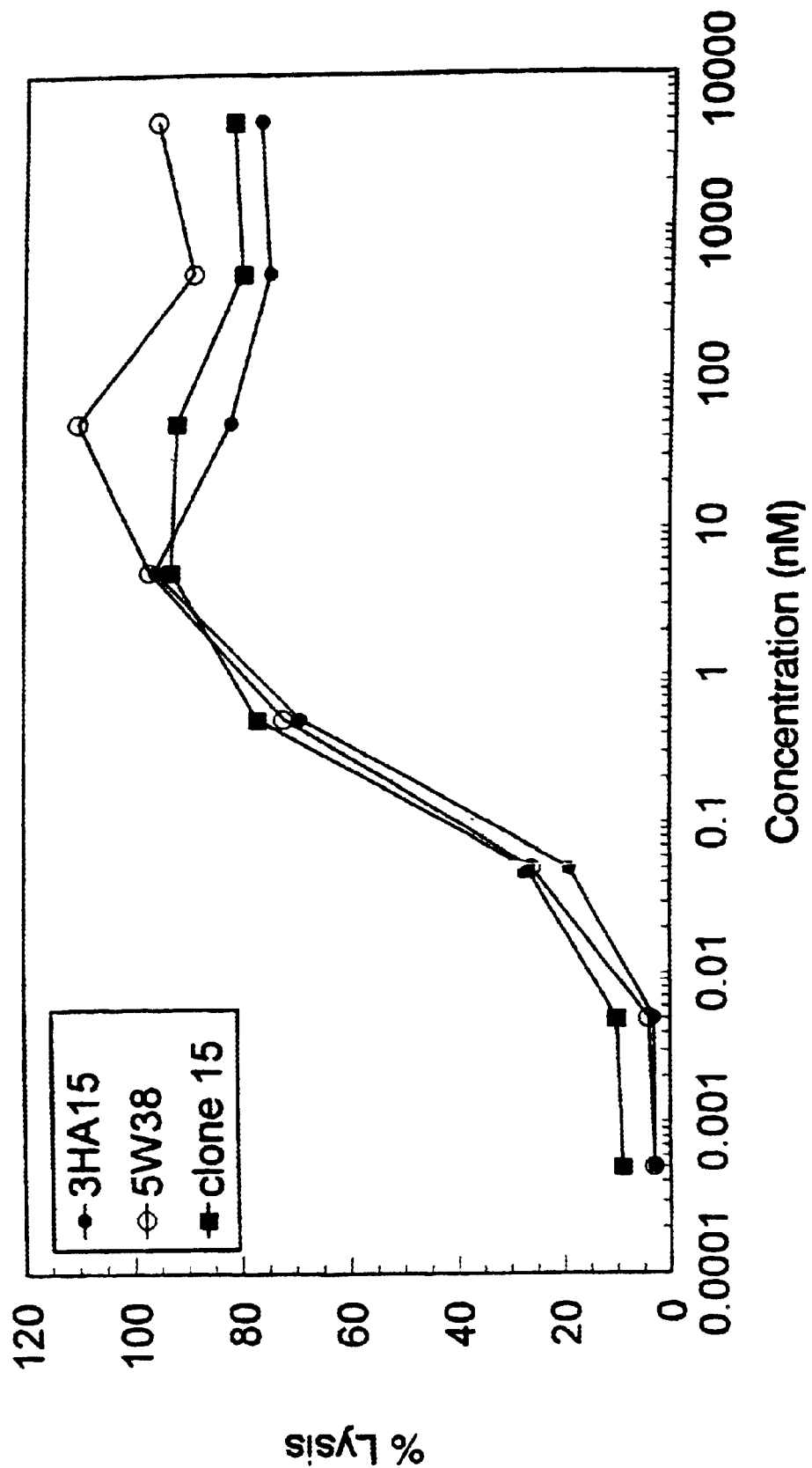

To identify the mH antigen HA-1, HLA-A2.1 molecules were purified from two HA-1 expressing EBV-transformed B lymophoblastoid cell lines (EBV-BLCL) Rp and Blk. The HLA-A2.1 bound peptides were isolated by acid treatment and fractionation of the peptides was performed by multiple rounds of reverse phase HPLC. The fractions were analysed for their capacity of inducing HA-1 specific lysis using T2 cells as target cells and an HA-1 specific CTL clone as effector cells in a $^{51}$Cr-release assay (FIG. 1a). Fraction 24 contained HA-1 activity and was two times further fractionated with reverse phase HPLC using a different organic modifier (FIG. 1b.c.). Fraction 33 and 34 of the third HPLC fractionation showed HA-1 activity $^{51}$Cr-release assay and were anlaysed by tandem mass spectrometry. Because over a 100 different peptides were present in these fractions, around 40% of fractions 33 and 34 was chromatographed with an on-line microcapillary column effluent splitter. The fractions were simultaneously analysed by tandem mass spectrometry and $^{51}$Cr-release assay (FIG. 1d). Five peptide species (at m/z 550, 520, 513, 585 and 502) were specifically present in active fractions and absent in fractions without activity in the CML assay. Collision activated dissociation analysis of peptide candidate m/z 550 revealed the sequence of YXTDRVMTV (SEQ ID NO: 36). X stands for isoleucine or leucine that cannot be discriminated with this type of mass spectrometer. However, a synthetic peptide with this sequence was not able to reconstitute the HA-1 epitope (results not shown). To determine which of the four remaining candidates was the HA-1 peptide the second HA-1 purification of the EBV-BLCL Blk was evaluated. HA-1 positive peptide fraction 33 of the second reverse phase HPLC fractionaction was further chromatographed by microcapillary HPLC with a third organic modifier. A single pair of reconstituting activity was observed in a $^{51}$Cr-release assay (results not shown). Mass spectral analysis of these fractions revealed that only peptide candidate m/z 513 was present. This peptide was analyzed with collision activated dissociation analysis and sequenced as VXHDDXXEA (SEQ ID NO: 37) (FIG. 2a). Isoleucine and Leucine variants of the peptide were synthesized and run on the microcapillary HPLC column. Only peptide VLHDDLLEA coeluted with the naturally processed peptide 513 (results not shown). Next, synthetic VLHDDLLEA added in different concentration to a CML assay with 3 different HA-1 specific CTL clones revealed recognition by all three clones of the peptide with a half maximal activity at 150–200 pM for all three clones (FIG. 2b). This demonstrated that the mH antigen is represented by the nonapeptide VLHDDLLEA.

Database searches performed to identify the gene encoding HA-1, revealed that the HA-1 peptide VLHDLLEA (SEQ ID NO: 38) was identical for 8 out of 9 amino acids with the peptide VLRDDLLEA from the KIAA0223 partial complementary DNA (cDNA) sequence, derived from the acute myelogenous leukemia KG-1 celline (GENBANK Acc No. D86976). Because HA-1 has a population frequency of 69%, we reasoned that the VLRDDLLEA peptide sequence might represent the HA-1 allele counterpart present in the remaining 31% of the population. To elaborate on this assumption, we performed cDNA sequence analysis of the putative HA-1 encoding region of KIAA0223 in EBV-BLCL derived from a presumed HA-1 homozygous positive (vR), from a presumed HA-1 negative individual (DH) and from the KG-1 cell line (Table 5). The HA-1 encoding region of KIAA0223 of the HA-1+/+ individual (vR) displayed two nucleotides differences from the KIAA0223 sequence in the databank, leading to the amino acid sequence VLHDDLLEA (designated HA-1$^H$). The HA-1 encoding region of KIAA0223 of the HA-1-/- individual (DH) showed 100% homology with the reported KIAA0223 sequence (designated HA-1$^R$). The KG-1 cell line expressed both KIAA0223 alleles. Because KG-1 does not express the restriction molecule HLA-A2.1 necessary for T cell recognition, we transfected KG-1 with HLA-A2.1 and used these cells as target cells in a $^{51}$Cr-release assay with the HA-1 specific T cell clone as effector cells. According to the cDNA sequence analysis results, the KG-1 cells were recognized by the HA-1 specific T cell clone (data not shown). This result suggested that the KIAA0223 gene forms a di-allelic system of which the HA-1$^H$ allele leads to recognition by the mH antigen HA-1 specific T cell clones.

Figure 3A:
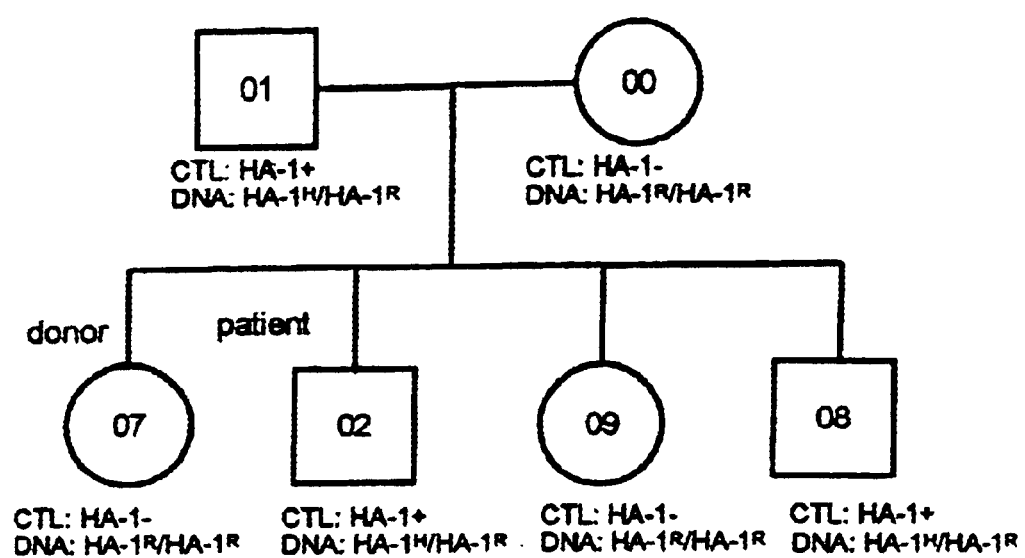
Figure 3B:
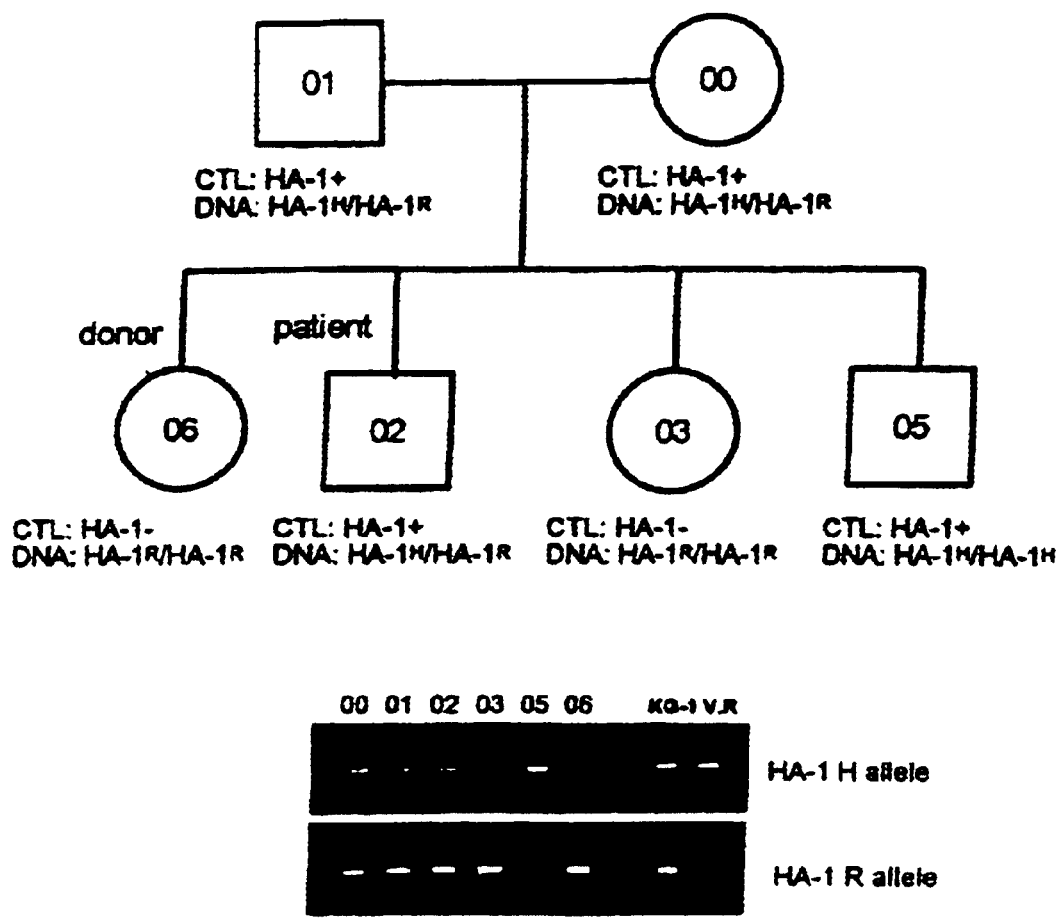

Two families, who were previously types for HA-1 with HA-1 specific CTL, were studied on the cDNA level for their KIAA0223 polymorphism. The family members of family 1, were screened for their KIAA0223 sequence polymorphism by sequencing the HA-1 encoding sequence region. All HA-1 negative members displayed the HA-1$^R$ sequence, whereas all HA-1 positive members turned out to be heterozygous, thus carrying both HA-1 alleles (FIG. 3a). We subsequently designed HA-1 allele specific PCR primers to screen another family previously cellularly typed for HA-1. Both parents and one child were determined as heteozygous for HA-1, two HA-1 negative children homozygous for the HA-1$^R$ allele and one child homozygous for the HA-1$^H$ allele (FIG. 3b). The screening of both families showed an exact correlation of the HA-1 phenotype as determined by recognition by the HA-1 specific T cell clones and the KIAA0223 gene polymorphism.

Figure 3C:
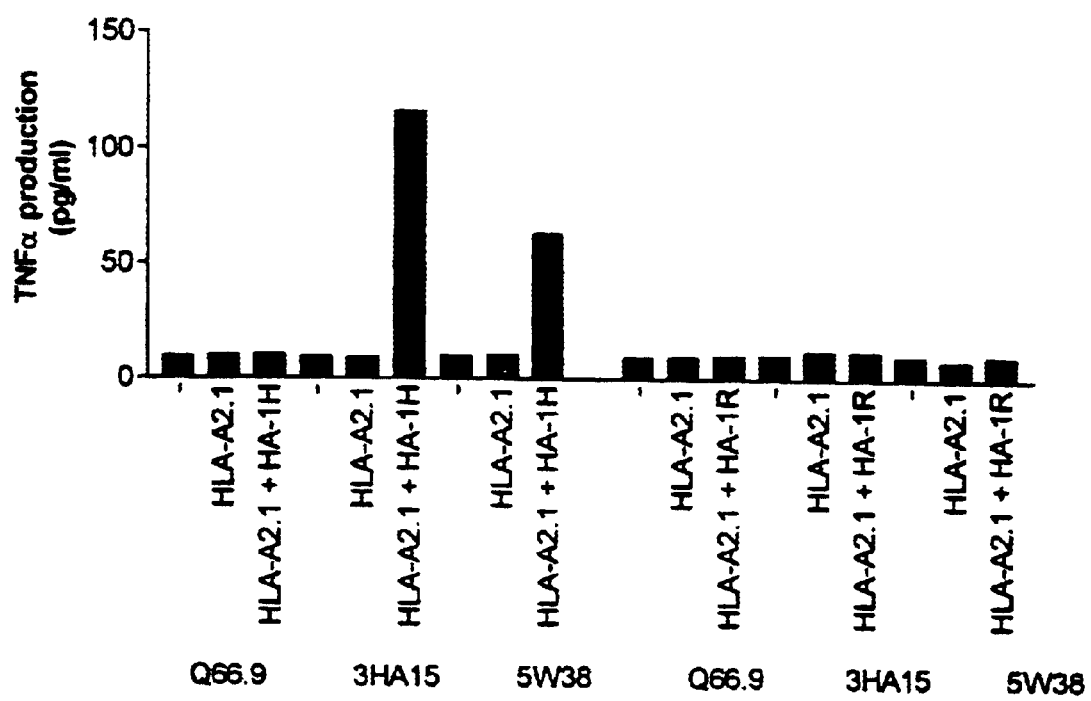

To definitely prove that the KIAA0223 gene encodes the mH antigen HA-1, the HA-1 encoding sequence region of KIAA0223 of both the HA-1$^H$ and the HA-1$^R$ alleles were cloned in a eukaryotic expression vector and transiently transfected in HA-1 negative Hela cells in combination with HLA-A2.1. HA-1 specific T cell recognition of these transfected Hela cells was assayed using a TNFα release assay. The Hela cells transfected with the HA-1$^H$ sequence containing vector were recognized by two HA-1 specific T cell clones (FIG. 3c). In contrast transfection of the HA-1$^R$ sequence containing vector did not lead to recognition. In conclusion, our results clearly demonstrate that the mH antigen HA-1 is encoded by the HA-1$^H$ allele of the KIAA023 gene.

Figure 4A:
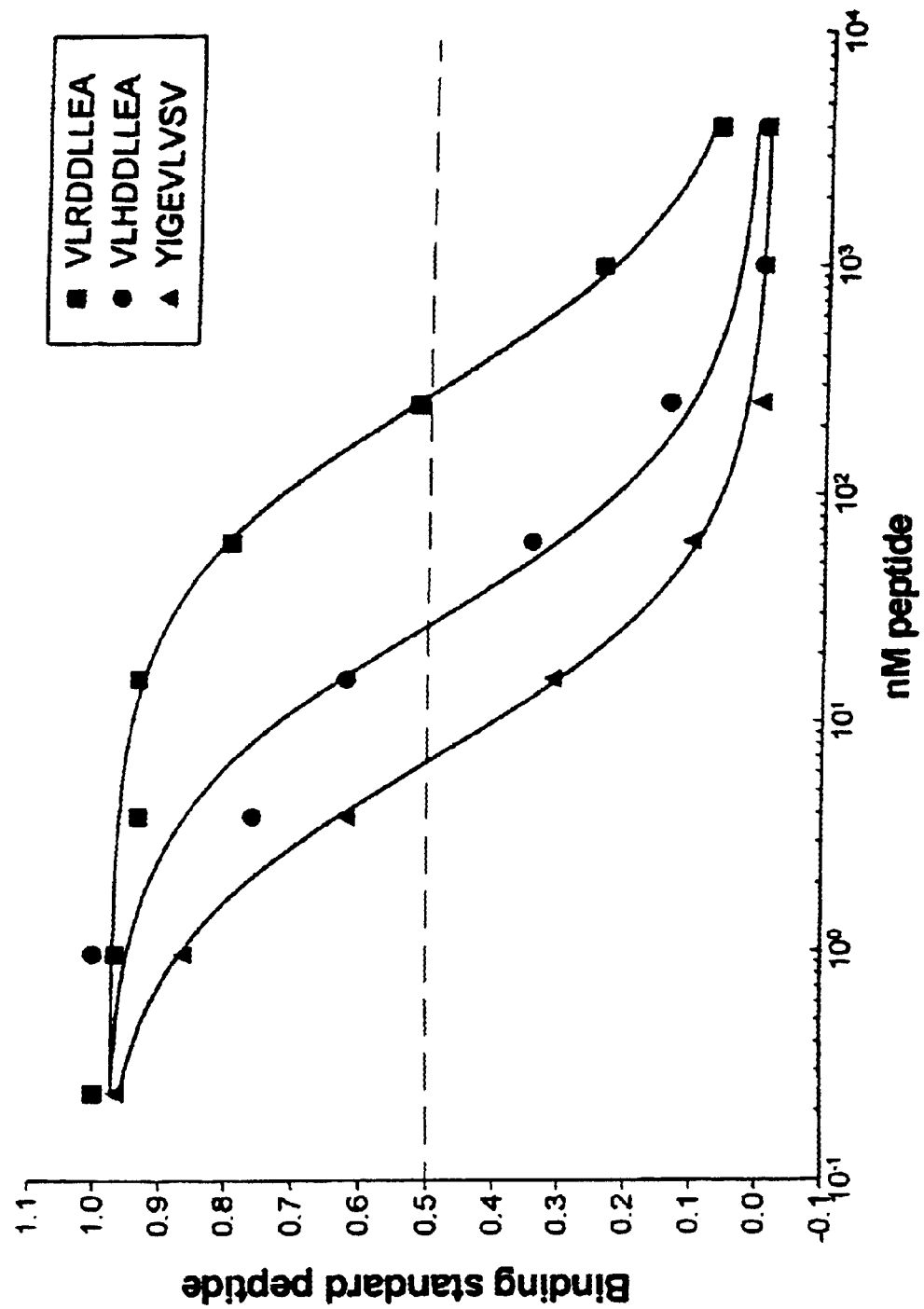
Figure 4B:
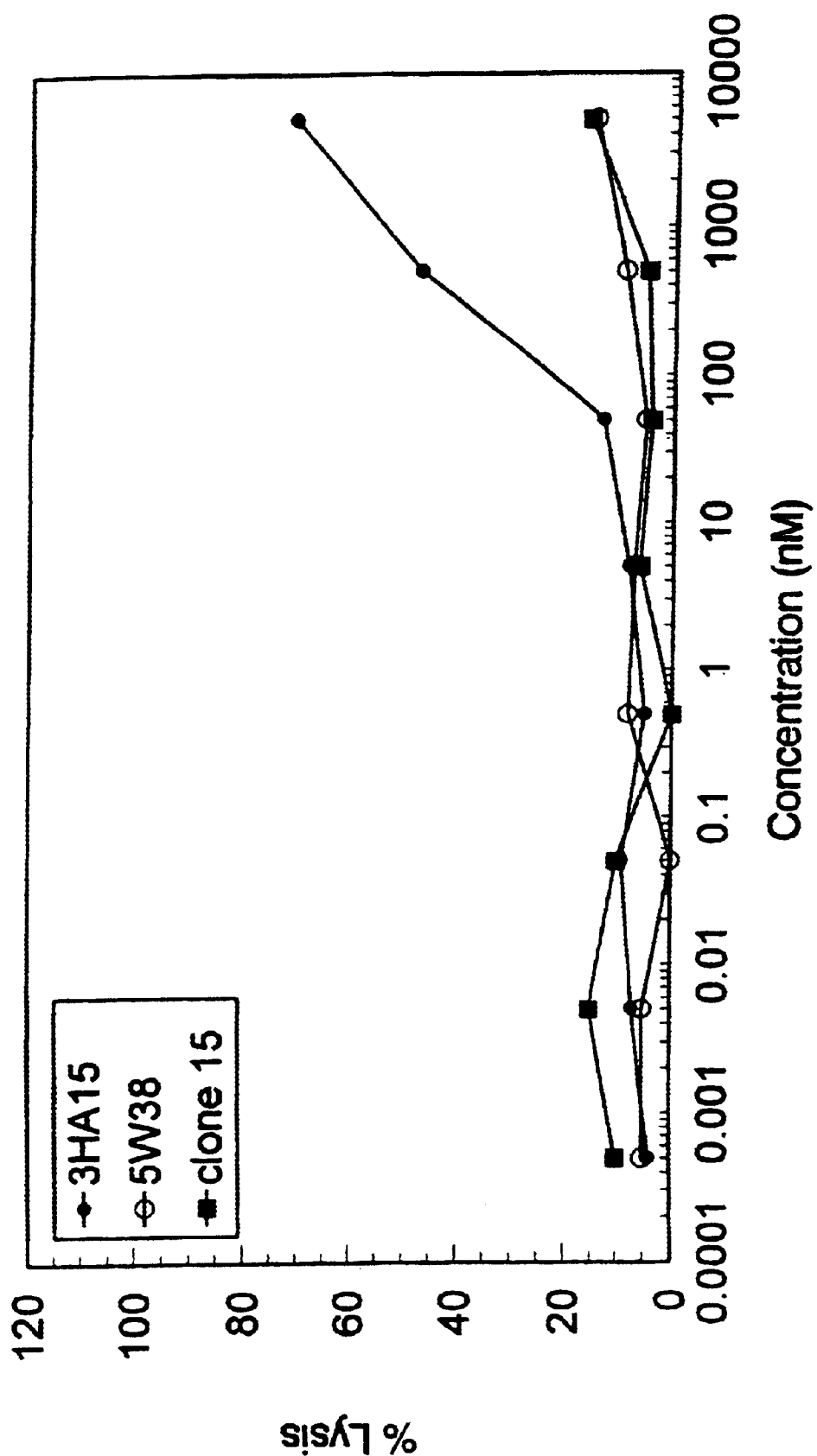

Reconstitution and HLA-A2.1 binding assays were performed to determine the capacity of HA-1$^R$ peptide VLRDDLLEA to bind to HLA-A2.1 and to be recognized by the HA-1 specific T cell clones. The concentration of the HA-1$^R$ peptide that inhibited the binding of a fluorescent standard peptide to HLA-A2.1 by 50% (IC50) was 365 nM, falling in the intermediate binders, whereas the IC50 of the HA-1$^H$ peptide was 30 nM, which is in the range of high affinity binders (FIG. 4a)[13,14]. Different concentrations of VLRDDLLEA were tested in a $^{51}$Cr-release assay with three HA-1 specific T cell clones. One out of three clones (3HA15) tested showed recognition of the HA-1$^R$ peptide, but only at 1000 times higher peptide concentration that the necessary for the recognition of the HA-1$^H$ peptide (FIG. 4b). As the binding affinity of the two peptides to HLA-A2.1 differs only 10-fold, it can be concluded that all the T cell clones specifically recognize the HA-1$^H$ peptide.

The 3HA15 T cell clone, recognizing the HA-1$^R$ peptide at high concentrations, does not recognize HA-1$^R$ homozygous individuals. This suggests that the VLRDDLLEA peptide is not presented by HLA-A2.1 or presented below the detection limit of the T cell. To determine whether the HA-1$^R$ peptide VLRDDLLEA was presented by HLA-A2.1, HLA-A2.1 bound peptides were eluted from a HA-1$^R$ homozygous EBV-BLCL and fractionated with reverse phase HPLC. The synthetic HA-1-peptide VLRDDLLEA was run on reverse HPLC to determine at which fraction this peptide eluted. The corresponding HPLC fractions derived from the HA-1$^R$ expressing EBV-BLCL were analysed using mass spectrometry. Presence of peptide VLRDDLLEA could not be detected (results not shown), indicating that this peptide is not or in very low amounts presented by HLA-A2.1 on the cell surface. This is most likely due to the 10-fold lower binding affinity of the peptide for HLA-A2.1. The supposed absence of the HA-1$^R$ peptide in HLA-A2.1 indicate that this allele must be considered as a null allele with regard to T cell reactivity. This implicates that only BMT from an HA-1$^{R/R}$ (HA-1-) donor to HA-1$^{R/H}$ or HA-1$^{R/H}$ (HA-1+) recipient direction and not the reverse would be significantly associated with GvHD. This is indeed observed in a retrospective study in which HLA-2.1 positive BMT pairs were typed for HA-1[3]. However, HA-1$^R$ derived peptides may bind to other HLA alleles and possibly be recognized by T cells. If the latter peptides are not generated and presented by the HA-1$^H$ allele, then T cell reactivity towards the HA-1$^R$ allele may be envisaged and GvHD in that direction may occur.

[3] (Sequence ID No.: 32)

Only a few murine and human mH antigens have been identified so far on the peptide and gene level. Two murine mH antigens are encoded by mitochondrial proteins, leading to respectively four and two alleles[15–17]. In addition, two minutes H-Y antigens were shown to be peptides encoded by Y-chromosome located genes [18-21]. The human SMCY gene, located on the Y chromosome, encodes the HLA-B7 and the HLA-A3.1 restricted H-Y mH antigens[3b]. Of the human non-sex linked mH antigens only the mH antigen HA-2 has been sequenced on the peptide level, but the HA-2 encoding gene remained unknown[4]. The identification of the gene encoding the mH antigen HA-1 is the first demonstration that human mH antigens are derived from polymorphic genes. The HA-1 encoding KIAA0223 gene has two alleles differing in two nucleotides leading to one single amino acid difference.

[4] (Sequence ID No.: 33)

Because the HA-1 mH antigen is the only known human mH antigen that is correlated with the development of GvHD after BMT the results of our study are of significant clinical relevance[3]. Although the numbers of different human mH antigens is probably high, it is envisaged that only few immunodominant mH antigens can account for the risk for GvHD[22]. Identification of those human immunodominant mH antigens and screening for those antigens may result in a significant decrease in GvHD after BMT. Here we describe the first elucidation of a polymorhpic gene encoding the immunodominant mH antigen HA-1. This enabled us to design HA-1 allele specific PCR primers for pre-transplant donor and recipient typing to improve donor selection and thereby prevention of HA-1 induced GvHD development.

[3] (Sequence ID No.: 32)

1.2 Methods 1.2.1 Cell culture.

The CD8+HLA-A2.1 restricted HA-1 specific cytotoxic T cell clones 3HA15, clone 15 and 5W38 were derived from PBMC of two patients who had undergone HLA identical bone marrow transplantation[7,23]. The clones were cultured by weekly stimulation with irradiated allogeneic PBMC and BLCL in RPMI-1640 medium containing 15% human serum, 3 mM 1-glutamin, 1% Leucoagglutinin-A and 20 U/ml rIL-2. The HLA-A2.1 positive HA-1 expressing EBV transformed B cell lines (BLCL) Rp and Blk were maintained in IMDM containing 5% FCS. The KG-1 and T2 cell lines were cultured in 1640 medium containing 3 mM 1-glutamin and 10% FCS.

1.2.2 $^{51}$Cr-release assay.

HPLC fractions and synthetic peptides were tested in a $^{51}$Cr-release assay as described[24]. 2500 $^{51}$Cr labeled T2 cells in 25 µl were incubated with 25 µl peptide dissolved in Hanks 50 mM Hepes for 30 minutes at 37° C. Cytotoxic T cells were added in an endvolume of 150 µl. When HPLC peptide fractions were tested, T2 was incubated with 2 µg/ml MA2.1 during the $^{51}$Cr labelling. After 4 hours at 37° C. the supernatants were harvested.

1.2.3 Peptide purification.

Peptides were elutated out of purified HLA-A2.1 molecules as earlier described [24]. Briefly, HLA-A2.1 molecules were purified two times from 90.10$^9$ HLA-A2.1 positive EBV-BLCl, by affinity chromatography with BB7.2 coupled CNBR-activated sepharose 4B beads (Pharmacia LKB) and extensively washed. Peptides were elutated from the HLA-A2.1 with treatment with 10% acetic acid, further acidified by 1% TFA and separated from the HLA-A2.1 heavy chain and β2-microglobulin by filtration over a 10 kD Centricon (Amicon) filter. Peptides were fractionated using reverse phase micro HPLC (Smart System, Pharmacia). For the first purification three rounds of HPLC fractionation were used to purify the HLA-A2.1 restricted HA-1 active peptide fractions from 90.10$^9$ Rp cells. The first fractionation consisted of buffer A: 0.1% HFBA in H2O, buffer B: 0.1% HFBA in acetonitrile. The gradient was 100% buffer A (0 to 20 min), 0 to 15% buffer B (20 to 25 min) and 15 to 70% buffer B (25 to 80 min) at a flow rate of 100 µl/min. Fractions of 100 µl were collected. Fraction 24 of the first gradient was further fractionated. The second fractionation consisted of buffer A: 0.1% TFA in H2O, buffer B: 0.1% TFA in acetonitrile. The gradient was 100% buffer A (0 to 20 min), 0 to 12% buffer B (20 to 25 min), and 12 to 50% buffer B (25 to 80 min) at a flow rate of 100 µl/min. Fractions of 100 µl were collected. A shallower third gradient was used to further purify fraction 27 that contained HA-1 activity. The gradient was 100% buffer A (0 to 29 min), 0 to 18% buffer B (29 to 34 min), 18% buffer B (34 to 39 min), 18 to 23.9% buffer B (39 to 98 min) at a flowrate of 100 µl/min. 1/180 to 1/45 of the starting material was used to test for positive fractions in the $^{51}$Cr-release assay. Comparable HPLC fractionations were used for the second purification of HLA-A2.1 restricted HA-1 active peptide fractions from 90.10$^9$ Blk. 40% of the HA-1 containing fraction 33 of the second HA-1 purification was used for an additional reverse phase microcapillary HPLC fractionation. Buffer A was 0.1% triethyl amine (TEA) in water buffered to pH 6.0 with acetic acid and buffer B was 0.085% TEA in 60% acetonitrile buffered to pH 6.0 with acetic acid. The gradient was 100% buffer A (0 to 5 min), 0 to 100% B (5 to 45 min) at a flow rate of 0.5 µl/min. Fractions were collected in 50 µl of 0.1% acetic acid every minute for 5 to 15 minutes, every 30 seconds from 15 to 20 minutes, every 20 seconds from 20 to 40 minutes, and every 30 seconds from 40 to 45 minutes. For each fraction collected, 20% was used to test for HA-1 activity and 80% was used to obtain mass spectral data.

1.2.4. Mass spectrometry.

Fractions from third dimension HPLC separation of the Rp purification that contained the HA-1 activity were analyzed by microcapillary HPLC-electrospray ionization mass spectrometry[25]. Peptides were loaded onto a C18 microcapillary column (75 µm i.d.×10 cm) and eluted with a 34 minute gradient of 0 to 60% B, where solvent A was 0.1M acetic acid in water and solvent B was acetonitrile at a flow-rate of 0.5 µl/min. One-fifth of the effluent was deposited into the wells of a 96-well plate containing 100 µl of culture media in each well (10 seconds fractions), while the remaining four-fifths was directed into the electrospray source of the TSQ-70U. Mass spectra and CAD mass spectra were recorded on a Finnigan-MAT TSQ-7000 (San Jose. Calif.) triple quadrupole mass spectrometer equipped with an electrospray ion source.

1.2.5 HLA-A2.1 peptide binding assay.

A quantitative assay for HLA-A2.1 binding peptides based on the inhibition of binding of the flourescent labeled standard peptide Hbc 18–27 F to C6 (FLPSDCFPSV) to recombinant HLA-A2.1 protein and β2-microglobulin was used [26,27]. In short, HLA-A2.1 concentrations yielding approximately 40–60% bound fluorescent standard peptide were used with 15 pmol/well (150 nM) β2-microglobulin (Sigma). Various doses of the test peptides were coincubated with 100 fmol/well (1 nM) fluorescent standard peptide. HLA-A2.1 and β2-microglobulin for 1 days at room temperature in the dark in a volume of 100 μl in assay buffer. The percent of MHC-bound fluoescence was determined by gel filtration and the 50% inhibitory dose was deduced for each peptide using one-site competition non-linear regression analysis with the prismgraph software. Synthetic peptides were manufactured on a Abimed 422 multiple peptide synthesizer (Abimed, Langenfeld, Germany) and were more than 90% pure as checked by reverse phase HPLC.

1.2.6. RT-PCR amplification and sequencing of KIAA0223 region coding for HA-1

Total or mRNA was prepared from BLCL using the RNAzol methode (Cinaa/Biotecx Laboratories, Houston, Tex.) or according to manufacturer's instructions (Quick-Prep mRNA purification Kit, Pharmacia Biotech). CNDA was synthesized with 1 μg RNA as template and with KIAA0223 based reverse primer 5'-GCTCCTGCAT-GACGCTCTGTCTGCA-3'[1]. To amplify the HA-1 region of KIAA0223 the following primers were used: Forward primer 5'-GACGTCGTCGAGGACATCTCCCAT-5'[2] and reverse primer 5'-GAAGGCCACAGCAATCGTCTC-CAGG-3'[3]. Cycle parameters used were denaturation 95° C., 1 min. annealing 58° C. 1 min and extension 72° C., 1 min (25 cycles). The PCR-products were purified using the Magic PCR-Preps DNA purification System (Promega) and direct cloned using the pMosBlue T-vector kit (Amersham LIFE SCIENCE). Six independent colonies from each individual were sequenced using the T7-sequencing kit (Pharmacia Biotech).

[1] (Sequence ID No.: 30)
[2] (Sequence ID No.: 31)
[3] (Sequence ID No.: 32)

1.2.7. HA-1 allele specific PCR amplification

In the case of HA-1 allele specific PCR amplification, cDNA was synthesized as described above. A PCR amplification was performed with allele specific forward primers: for the HA-1$^H$ allele primer H1:5'-CCT-TGA-GAA-ACT-TAA-GGA-GTG-TGT-GCT-GCA-3'[4], for the HA-1$^R$ allele primer R1:5'-CCT-TGA-GAA-ACT-TAA-GGA-GTG-TGT-GTT-GCG-3'[5] and for both reaction the reverse primer as described above was used. Cycle parameters used were denaturation 95° C., 1 min. annealing 67° C., 1 min and extension 72° C. 1 min (25 cycles).

[4] (Sequence ID No.: 33)
[5] (Sequence ID No.: 34)

1.2.8. Cloning and expression of HA-1$^H$ and HA-1$^H$ allelic region of KIAA0223.

A forward KIAA00223 based PCR primer containing an ATG startcodon (5'-CCG-GCA-TGG-ACG-TCG-TCG-AGG-ACA-TCT-CCC-ATC-3' (SEQ ID NO:23)) and a reverse KIAA0223 based PCR primer containing a translational stop signal (5'-CTA-CTT-CAG-GCC-ACA-GCA-ATC-GTC-TCC-AGG-3'(SEQ ID NO:24)) were designed and used in a RT-PCR reaction with cDNA derived from an homozygous HA-1$^H$ and a homozygous HA-1$^H$ BLCL. Cycle parameters used were denaturation 95° C. 1 min. annealing 60° C., 1 min and extension 72° C., 1 min (25 cycles). The desired PCR-products were purified using the Magic PCR-Preps DNA purification System (Promega). The purified DNA was direct cloned using the pMosBlue T-vector kit (Amersham LIFE SCIENCE) and recloned in the eukaryotic pCDNA3.1(+) vector under the control of a CMV promoter. Transient cotransfections were performed with HLA-A2.1 in Hela cells using DEAE-Dextran coprecipitation. After 3 days of culture HA-1 specific T cells were added and after 24 hours the TNFα release was measured in the supernatant using WHEI cells[28].

2. Example 2

Materials and methods for economic DNA isolating of HA-1 alleles

Cell culture and isolation of genomic DNA:

Genomic DNA was isolated from frozen peripheral blood lymphocytes (PBL) with the High Pure Temperature Purification Kit from Boehringer Mannheim according to the manufacturers description. EBV-transformed LCLs cells were cultured in RPMI-1640 containing 3 mM L-glutamine an d10% FCS. For DNA isolation the cells were harvested, washed twice with phosphate buffered saline (PBS), resuspended in 200 μl and kept at −20C until use. For each DNA isolation 2×10$^6$ cells were used.

Genomic PCR:

For each PCR reaction 100–200 ng of genomic DNA were used. Amplifications were performed with 20 pmol of each primer in 100 μl of 10 mM Tris/HCl (pH8.4) buffer, containing 50 mM KCl, 4 mM MgCl2 , 0.06 mg/ml BSA, 0.5 mM dNTP's and 2.5 units Taq polymerase (Roche Molecular Systems, Brancheburg, N.J.). All reactions started with a denaturation step of 5 min. at 95° C. The cycling conditions for all primer combinations were 95° C. for 1 min. and 65° C. for 1 min. for ten cycles. Followed by 20 cycles at 95° C. for 1 min., 65° C. for 1 min., 75° C. for 1 min., and an extension of the last step for 5 min. at 75° C.

Isolation of cosmid DNA:

For the large scale isolation of cosmid DNA, 11 of LB-medium (20 μg/ml Ampicillin) was inocculated and grown overnight at 37° C. with vigorous shaking (300 rpm). The cosmid DNA was isolated by using the low-copy number plasmid isolation protocol of the Quiagen Plasmid Purification Kit according to the manufacturers description. This isolation method yielded on average in 500 μg of purified cosmid DNA.

Sequencing of cosmid DNA:

For each sequencing reaction. 10 μg of cosmid DNA. The sequencing reactions were performed with the T7 Sequencing kit (Pharmacia Biotech).

mHag HA-1 specific CTL:

EBV-transformed-LCLs were tested with HA-1 specific CTLs. Reactivity was determine by a chromium release assay. $^{31}$Cr labelled target cells (3×10$^5$) were co-incubated with serial dilutions of effector T-cells in 96 well round bottom microtiter plates (Costar 3799). After 4 hours at 37° C. cell free supernatants were harvested for gamma counting. The percent specific lysis was calculated as follows: 5 specific lysis=(experimental release-spontaneous release)/ (maximal release-spontanous release)×100%. Spontanous release and maximum release are the chromium release of target cells in culture medium alone and in culture medium containing 1% Triton-X100, respectively.

3. Example 3

The HA-1 peptide is encoded by two exons

For the determination of the genomic structure surrounding the HA-1 peptide a cosmid library derived from human male PBLs was screened. The 312 bp cDNA fragment encoding the HA-1 peptide was used as probe for screening. Three overlapping cosmids were isolated. The cosmid pTCF-HA-1 containing the R-allele was partially sequenced. The sequence reaction revealed a splice donor site four nucleotides after the HA-1 polymorphic codon. A splice acceptor site could be identified in front of the second exon coding for the HA-1 peptide (FIG. 5). Thus, the HA-1 peptide sequence is encoded by two exons.

4. Example 4

Allele-specific PCR on genomic DNA

For the genomic allele-specific typing two different primer sets were designed. Both sets do contain a common primer and one specific for either the HA-1 H-allele or R-allele (table 1). The common primer of set 1 is derived from the exon encoding the first four amino acids of the HA-1 peptide. The H/R primers contain intronic sequences, the splice donor site and the allele specific part of the exon sequence. Set 2 consists of a common primer derived from the intran identified in pTCF-HA-1 and exon derived primers covering the H- and R-allele. Amplification with primer set 1 resulted in a 190 bp fragment, primer set 2 gave a 331 bp fragment. Both primer sets showed the expected length of fragments and are suitable for genomic typing. Because the primers were chosen in such a way, that they should amplify the DNA under identical PCR conditions, a combination of both primer sets can be used in the same PCR reaction. In this case, a third fragment of 535 bp was observed due the amplification of the DNA between the two different common primers (data not shown).

5. Example 5

Family studies

The feasibility of genomic typing was carried out on 24 members belonging to three HLA-A*0201 positive families. The results of the DNA typing was compared with the mHag HA-1 CTL typing (table 3) and showed an exact correlation. FIG. 6 shows the genomic DNA analysis of the HA-1 locus in a representative family. The bone marrow donor (06) and recipient (02) were HLA-identical. The donor was homozygons for the R-allele. The recipient was heterozygous (H/R) and therefore presenting the HA-1 antigen at the cell surface. This mismatch resulted in GvHD, thus the T-cells of the donor reacted against the mHag of the recipient. In this family the donor and recipient were HLA-identical, but they had a mismatch in the HA-1 sequence. The same disparities for HA-1 could be observed in family 2. Again the donor (07) was homozygous for the R-allel and the patient (02) was heterozygous (H/R), resulting in GvHD. Family 3 represents the segregation of the HA-1 H-allele in three generations in an healthy family. The H-allele is derived from the grandfather (01) and is inherited by two generations. The grandmother (00) although HLA-A*0201 positive is homozygous for the R-allele. Their children (03, 04, and 05) are all heterozygous for the HA-1 locus. The child 04 married individual 34 who is HLA-A*0201 positive, but homozygous for the R-allele. From their offspring, only 84 inherited the HA-1 H-allele from the grandfather. The other grandchildren (82, 83 and 85) are HA-1 R homozygous.

TABLE 3

Cellular and genomic typing for HA-1 in three HLA-A*0201 positive families

|  | CML analysis | PCR analysis |
|---|---|---|
| Family 1 | | |
| 00 | + | H/R |
| 01 | + | H/R |
| 02* | + | H/R |
| 03 | − | R/R |
| 05 | + | H/H |
| 06* | − | R/R |
| Family 2 | | |
| 00 | − | R/R |
| 01 | + | H/R |
| 02* | + | H/R |
| 04 | + | H/R |
| 06 | + | H/R |
| 07* | − | R/R |
| 09 | − | R/R |
| 10 | + | H/R |
| Family 3 | | |
| 00 | − | R/R |
| 01 | + | H/R |
| 03 | + | H/R |
| 04 | + | H/R |
| 05 | + | H/R |
| 34 | − | R/R |
| 82 | − | R/R |
| 83 | − | R/R |
| 84 | + | H/R |
| 85 | − | R/R |

6. Example 6

Typing of HA-1 alleles by the LiPA method

The following method for typing of the HA-1 alleles H and R in a sample, is based on the LiPA technology (Stuyver et al., 1993). For each PCR reaction 100–200 ng of genomic DNA is used. Amplifications are performed with 20 pmol of each primer in 100 μl of 10 mM Tris/HCl (pH8.4) buffer, containing 50 mM KCl, 4 mM MgCl2, 0.06 mg/ml BSA, 0.5 mM dNTP's and 2.5 units Taq polymerase (Roche Molecular Systems, Brancheburg, N.J.). All reactions start with a denaturation step of 5 min. at 95° C. The cycling conditions for all primer combinations are 95° C. for 1 min. and 65° C. for 1 min. for ten cycles. Followed by 20 cycles at 95° C. for 1 min., 62° C. for 1 min., 72° C. for 1 min., and an extension of the last step for 5 min. at 72° C. The HA-1 alleles are subsequently typed by a reverse hybridization step to oligonucleotide probes that are immobilized on a nine-cellulose strip. Probes specifically hybridizing to the R-allele are for instance HA1-R1(1) (SEQ ID NO 11), HA1-R1(2) (SEQ ID NO 12). and HA1-R1(3) (SEQ ID NO 13). Probes specifically hybridizing to the H-allele are for instance HA1-H1(1) (SEQ ID NO 14), HA1-H1(2) (SEQ ID NO 15) and HA1-H1(3) (SEQ ID NO 16). The hybridization is performed in 5×SSPE, 0.5% SDS at 56° C. for 30 min. A stringent washing step is carried out in 2×SSPE, 0.1% SDS at 56° C. for 10 min. A LiPA containing the specific probes HA1-H1(3) (SEQ ID NO 14), HA-1-R1(3) (SEQ ID NO 13) and a probe to control the colorimetric reaction (CC), was tested for feasibility with the 6 samples from family 1. The results obtained by LiPA (FIG. 7) confirmed the genomic typing results by PCR and the CTL typing (table 4).

TABLE 4 comparison of cellular and genomic typing
by PCR or LiPA of HA-1 in family 1.

| Family 1 | CML analysis | PCR analysis | LiPA analysis |
|---|---|---|---|
| 00 | + | H/R | H/R |
| 01 | + | H/R | H/R |
| 02 | + | H/R | H/R |
| 03 | − | R/R | R/R |
| 05 | + | H/H | H/H |
| 06 | − | R/R | R/R |

REFERENCES

1. Beatty, P. G. et al. Marrow transplantation from HLA-matched unrelated donors for treatment of hematologic malignancies. *Transplantation* 54, 443–447 (1997).
2. Marks, D. I. et al. Allogeneic bone marrow transplantation for chronic myeloid leukemia using sibling and volunteer unrelated donors. A comparison of complications in the first 2 years. *Ann. Intern. Med.* 119, 207–214 (1993).
3. Goulmy, E. et al. Mismatches of minor histocompatibility antigens between HLA-identical donors and recipients and the development of graft-versus-host disease after bone marrow transplantation. *N. Engl. J. Med.* 334, 285–285 (1996).
4. den Haan, J. M. et al. Identification of a graft versus host disease-associated human minor histocompatibility antigen. *Science* 268, 1476–1480 (1995).
5. Wang, W. et al. Human H-Y: a male-specific histocompatibility antigen derived from the SMCY protein [see comments]. *Science* 269, 1588–1590 (1995).
6. Meadows, L. et al. The HLA-A*0201-restricted H-Y antigen contains a postranslationally modified cysteine that significantly affects T cell recognition. *Immunity*, 6, 273–281 (1997).
7. van Els, C. A. et al. Immunogenetics of human minor histocompatibility antigens: their polymorphism and immunodominance. *Immunogenetics* 35, 161–165 (1992).
8. de Bueger, M., Bakker, A., van Rood, J. J., Van der Woude, R. & Goulmy, E. Tissue distribution of human minor histocompatibility antigens. Ubiquitous versus restricted tissue distribution indicates heterogeneity among human cytotoxic T lymphocyte-defined non-MHC antigens. *J. Immunol.* 149, 1788–1794 (1992).
9. Van Lochem, E., van der Keur, M., Mommaas, A. M., de Gast, G. C. & Goulmy, E. Functional expression of minor histocompatibility antigens on human peripheral blood dendritic cells and epidermal Langerhans cells. *Transpl. Immunol.* 4, 151–157 (1996).
10. van der Harst. D. et al. Recognition of minor histocompatibility antigens on lymphocytic and myeloid leukemic cells by cytotoxic T-cell clones. *Blood* 83, 1060–1066 (1994).
11. Schreuder. G. M. et al. A genetic analysis of human minor histocompatibility antigens demonstrates Mendelian segregation independent of HLA. *Immunogenetics* 38, 98–105 (1993).
12. Goulmy, E., Pool, J. & van den Elsen, P. J. Interindividual conservation of T-cell receptor beta chain variable regions by minor histocompatibility antigen-specific HLA-A*0201-restricted cytotoxic T-cell clones. *Blood* 85, 2478–2481 (1995).
13. Ruppert, J., Sidney, J., Celis, E. Kubo, R. T. Grey, H. M. & Sette, A. Prominent role of secondary anchor residues in peptide binding to HLA-A2.1 molecules. *Cell* 74, 929–937 (1993).
14. Chen, Y. et al. Naturally processed peptides longer than nine amino acid residues bind to the class 1 MHC molecule HLA-A2.1 with high affinity and in different conformations. *J. Immunol.* 152, 2874–2881 (1994).
15. Loveland, B., Wang, C. R., Yonekawa, H., Hermel, E. & Lindahl, K. F. Maternally transmitted hisuocompatilibity antigen of mice: a hydrophobic peptide of a mirochondrially encoded protein. *Cell* 60, 971–980 (1990).
16. Loveland, B. E., Fischer Lindahl, K. The definition and expression of minor histocompatibility antigens. McCluskey J, editors. Antigen processing and recognition. London: CRC Press, 9, 173–92 (1991).
17. Lindahl, K. F. Minor histocompatibility antigens. *Trends, Genet.* 7, 219–224 (1991).
18. Perreault, C., Jutras, J., Roy, D. C., Filep, J. G. & Brochu, S. Indentification of an immunodominant mouse minor histocompatibility antigen (MiHA). T cell response to a single dominant MiHA causes graft-versus-host disease. *J. Clin. Invest.* 98, 622–628 (1996).
19. Morse, M. C. et al. The COI mitochondrial gene encodes a minor histocompatibility antigen presented by H2-M3. *J. Immunol.* 156, 3301–3307 (1996).
20. Scott, D. M. et al. Identification of a mouse male-specific transplantation antigen, H-Y, *Nature* 376, 695–698 (1995).
21. Greenfield, A. et al. An H-YDb epitope is encoded by a novel mouse Y chromosome gene. *Nat. Genet.* 14, 474–478 (1996).
22. Manin, P. J. Increased disparity for minor histocompatibility antigens as a potential cause of increased GVHD risk in marrow transplantation from unrelated donors compared with related donors. *Bone Marrow Transplant.* 8, 217–223 (1991).
23. Goulmy, E., Gratama, J. W., Blokland, E., Zwaan, F. E. & van Road, J. J. A minor transplantation antigen detected by MHC-restricted cytotoxic T lymphocytes during graft-versus-host disease. *Nature* 302, 159–161 (1983).
24. de Bueger, M. et al. Isolation of an HLA-A2.1 extracted human minor histocompatibility peptide, *Eur. J. Immunol.* 23, 614–618 (1993).
25. Hunt, D. F. et al. Characterization of peptides bound to the class 1 MHC molecule HLA-A2.1 by mass spectrometry. *Science* 255, 1261–1263 (1992).
26. Ottenhoff, T. H. M. Geluk, A., Toebes, M., Benckhuijsen, W. E. van Meijgaarden, K. E. & Drijfhout, J. W. A sensitive fluorometric assay for quantitatively measuring specific peptide binding to HLA class I and class II molecules. *J. Immunol. Methods* 200, 89–97 (1997).
27. Tan, T. L. R., Geluk, A., Toebes, M., Ottenhoff, T. H. M. & Drijfhout, J. W. A novel, highly efficient peptide-HLA class I binding assay using unfolded heavy chain molecules; identification of HIV-1 derived peptides that bind to HLA-A*0201 and HLA-A*0301. Submitted (1997).
28. Traversari, C. et al. Transfection and expression of a gene coding for a human melanoma antigen recognized by autologous cytolytic T lymphocytes. *Immunogenetics* 35, 145–152 (1992).

Asseline U., Delarus M., Lancelot G. Touhne F, Thuong N (1984) Nucleic acid-binding molecules with high affinity and base sequence specificity : intercalating agents covalently linked to oligodeoxynucleotides. *Proc. Natl. Acad. Sci. USA* 81(11):3297–301.

Bej A., Mahbubani M., Miller R., Di Casare J., Haff L., Atlas R. (1990) Multiplex PCR amplification and immobilized capture probes for detection of bactarial pathogens and indicators in water. Mel Cell Probes 4:353–365.

Compton J. (1991) Nucleic acid sequence-based amplification. *Nature* 350: 91–92. Duck P. (1990) Probe amplifier system based on chimeric cycling oligonucleotides, Biotechniques 9: 142–147.

Guatelli J., Whitefield K, Kwoh D., Barringer K, Richman D. Gangeras T. (1990) Isothernal, in vitro amplification of nucleic acids by a multienzyme reaction modeled after retroviral replication. *Proc. Natl. Acad. Sci USA* 87: 1874–1878.

Kwoh D. Davis G. Whitefield K., Chappelle, H., Dimichele L., Gingeras T. (1989) Transcription-based amplification system and detection of amplified human immunodeficiency virus type 1 with a bead-based sandwich hybridization format. *Proc. Natl. Acad. Sci. USA* 86: 1173–1177.

Kwok S., Kellogg D., McKinney N. Spasic D. Goda L., Levenson C., Sinisky J. (1990). Effects of primer-template mismatches on the polymerase chain reaction: Human immunodeficiency virus type 1 model studies. *Nucl. Acids Res.* 18: 999.

Landgren U., Kaiser R., Sanders J., Hood L. (1988) A ligase-mediated gene detection technique. *Science* 241:1077–1080.

Lomeli H., Tyagi S., Pritchard C., Lasardi P., Kramer F. (1989) Quantitative assays based on the use of replicatable hybridization probes. *Clin. Chem.* 35: 1826–1831.

Matsukura M., Shinozuka K., Zon G., Mitsuya H., Reitz M., Cohen J., Broder S. (1987) Phosphorothioate analogs of oligodeoxynucleotides : inhibitors of replication and cytophathic effects of human immunodeficiency virus. *Proc. Natl. Acad. Sci. USA* 84(21):7706–10.

Miller P., Yano J., Yano E., Carroll C., Jayaram K., Ts'o P ( 1979) Nonionic nucleic acid analogues. Synthesis and characterization of dideoxyribonucleoside methyphosphonates, Biochemistry 18(23):5134–43.

Mullis K., Faloona F., Scharf S., et al. Specific enzymatic amplification of DNA in vitro: the polymerase chain reaction (1986). *Gold Spring Harb. Symp. Quant. Biol.* 1:263–273.

Mullis K. B. and Faloona F. A. Specific synthesis of DNA in vitro via a polymerase-catalyzed chain reaction (1987). *Methods Enzymol.* 155:335–350.

Nielsen P., Egholm M., Berg R., Buchardt O (1991) Sequence-selective recognition of DNA by strand displacement with a thymine-substituted polyamide. *Science* 254(5037):1497–500.

Nielsen P., Egholm M., Berg R., Buchardt O. (1993) Sequence specific inhibition of DNA restriction enzyme cleavage by PNA. Nucleic-Acids-Res. 21(2):197–200.

Santamaria P., Boyce J. M. Lindstrom A. L., et al. HLA class II "typing": direct sequencing of DRB, DQB and DQA genes (1992). *Hum. Immunol.* 33: 69–81.

Saiki R. K., Bugawan T. L., Horn G. T. et al., Analysis of enzymatically amplified beta-globin and HLA-DQ alpha DNA with allele-specific oligonucleotide probes (1985). *Nature* 324: 163–166.

Saiki R. K., Walsh P. S., Lavenson, C. H. and Erlich H. A. Genetic analysis of amplified DNA with immobilized sequence-specific oligonucleotide probes (1989). *Proc. Natl. Acad. Sci. USA* 86: 6230–6234.

Sambrook J., Fritsch E., Maniatis T. (1989) Molecular cloning: a laboratory manual. Cold Spring Harbor Laboratory Press, Cold Spring Harbor, N.Y.

Spencer Wells R. Parham P: HLA class I genes: structure and diversity. Chapter 4. HLA and MHC: genes, molecules and function, 1996 BIOS Scientific Publishers Ltd. Oxford.

Stuyver L., Rossau R., Wyseur A. et al. (1993) Typing of hepatitis C virus isolates and characterization of new subtypes using a line probe assay. *J. Gen. Virol.* 74: 1093–1102.

Terasaki R. H. and McClelland, J. D. Microdoplet assay of human serum cytotoxins. (1964) *Nature* 204: 998–1007.

Wu D., Wallace B. (1989) The ligation amplification reaction (LAR)—amplification of specific DNA sequences using sequential rounds of template-dependent ligation. *Genomics* 4:560–569.

TABLE 5

| Cell | CTL analysis HA-1 phenotype | KIAA0223 sequence | Nr. of clones sequenced | DNA analysis HA-1 phenotype |
|---|---|---|---|---|
| DH | HA-1 −/− | GAGTGTGTGTTGCGTGACGACCTCCTTGAGGCCCGCCG<br>E C V L R D D L L E A R R | (6/6 clones) | HA-1$^R$/HA-1$^R$ |
| vR | HA-1 +/+ | GAGTGTGTGCTGCATGACGACCTCCTTGAGGCCCGCCG<br>E C V L K D D L L E A R R | (6/6 clones) | HA-1$^H$/HA-1$^H$ |
| KG-1 | HA-1 + | GAGTGTGTGTTGCGTGACGACCTCCTTGAGGCCCGCCG<br>E C V L R D D L L E A R R | (1/8 clones) | HA-1$^R$/HA-1$^H$ |
|  |  | GAGTGTGTGCTGCATGACGACCTCCTTGAGGCCCGCCG<br>E C V L K D D L L E A R R | (7/8 clones) |  |

What is claimed is:

1. Method for typing of alleles of the Minor Histocompatibility Antigen HA-1 in a sample, the method comprising detecting polymorphic nucleotides in the cDNA or genomic nucleic acids of said alleles, thereby typing the alleles, wherein said alleles are HA-1H or HA-1R alleles, or a combination thereof with a sequence as shown in SEQ ID NOS 17 or 19.

2. Method for genomic typing according to claim 1, the method comprising:
   a. contacting the genomic polynucleic acids in the sample with at least one pair of primers, whereby the 5'- and/or the 3'primer of said at least one pair of primers specifically hybridize to target regions comprising polymorphic nucleotides in said alleles, and performing an amplification reaction;
   b. for each of said at least one pair of primers detecting whether or not in step a. an amplification product is formed;
   c. inferring from the result of step b. which HA-1 allele is present in said sample.

3. Method according to claim 2, wherein the at least one pair of primers comprises a 5'-primer that specifically hybridizes to a target region comprising the nucleotides at position 4 or at positions 4 and 8 in the HA-1 allele, or said at least one pair of primers comprises a 3'-primer that specifically hybridizes to a target region comprising the nucleotides at position 8 or at positions 4 and 8 in the HA-1 allele, with said positions being indicated in SEQ ID NOS 17 and 19.

4. Method according to claim 3, wherein the 5'-primer is combined with a 3'-primer specifically hybridizing to a target region in intron a, and/or the 3'-primer that specifically hybridizes to a target region comprising the nucleotides at postion 8 or at positions 4 and 8 in the HA-1 allele is combined with a 5'-primer specifically hybridizing to a target region in exon a, with intron a and exon a being indicated in SEQ ID NOS: 21–22.

5. Method according to claim 4, wherein the primers are SEQ ID NO 2, SEQ ID NO 3, SEQ ID NO 4, SEQ ID NO 5, SEQ ID NO 6, or SEQ ID NO 7.

6. Method for genomic typing according to claim 1, the method comprising:
   a. amplifying a fragment of said alleles, with said fragment comprising at least one polymorphic nucleotide, by use of at least one pair of primers specifically hybridizing to conserved target regions in said alleles;
   b. hybridizing the amplified product of step a. to at least one probe specifically hybridizing to a target region comprising one or more polymorphic nucleotides in said allele;
   c. inferring from the result of step b. which HA-1 allele is present in said sample.

7. Method according to claim 6, wherein the at least one pair of primers comprises a 5'-primer specifically hybridizing to a conserved target region in exon a and/or a 3'-primer specifically hybridizing to a conserved target region in intron a, with exon a and intron a being indicated in SEQ ID NOS: 21–22.

8. Method according to claim 6, wherein the at least one probe specifically hybridizes to a target region comprising the nucleotides at position 8 and/or 4 in the HA-1 allele, with said positions being indicated in SEQ ID NOS 17 and 19.

9. Method according to claim 6, wherein the primers are SEQ ID NO 2, SEQ ID NO 8, SEQ ID NO 9, or SEQ ID NO 10, and/or the probes are SEQ ID NO 11, SEQ ID NO 12, SEQ ID NO 13, SEQ ID NO 14, SEQ ID NO 15, or SEQ ID NO 16.

10. An isolated nucleic acid molecule consisting of the sequence of SEQ ID NO 1, SEQ ID NO 17, or SEQ ID NO 19 or the complement of SEQ ID NO 1, SEQ ID NO 17, or SEQ ID NO 19.

11. A method for genomic typing of alleles of the Minor Histocompatibility Antigen HA-1 according to claim 1 by means of sequencing said allele.

12. A kit comprising an isolated nucleic acid molecule consisting of the sequence of SEQ NOS 1, 17 or 19 or the complement of SEQ ID NOS 1, 17 and 19.

13. A diagnostic kit comprising:
  a. at least one primer, wherein the primer is SEQ ID NOS 2, 8, 9 or 10;
  b. at least one probe, wherein the probe is SEQ ID NOS 11, 12, 13, 14, 15 or 16;
  c. optionally, an enzyme and/or reagents enabling the amplification reaction, and/or reagents enabling the hybridization reaction.

14. A diagnostic kit comprising:
  a. at least one primer wherein the primer is SEQ ID NOS 2, 8, 9, or 10; and
  b. optionally, an enzyme and/or reagents enabling the amplification reaction, and/or reagents enabling the sequencing reaction.

15. An isolated nucleic acid molecule consisting of the sequence of SEQ ID NO: 2, SEQ ID NO: 8, SEQ ID NO: 9, or SEQ ID NO: 10 or the complement of SEQ ID NO: 2, SEQ ID NO: 8, SEQ ID NO: 9, or SEQ ID NO:10.

16. An isolated nucleic acid molecule consisting of the sequence of SEQ ID NO 11, SEQ ID NO 12, SEQ ID NO 13, SEQ ID NO 14, SEQ ID NO 15, or SEQ ID NO 16 or the complement of SEQ ID NO 11, SEQ ID NO 12, SEQ ID NO 13, SEQ ID NO 14, SEQ ID NO 15 or SEQ ID NO 16.

17. An isolated nucleic acid molecule consisting of the sequence of SEQ ID NO 3, SEQ ID NO 4, SEQ ID NO 5, SEQ ID NO 6, SEQ ID NO 7, or the complement of SEQ ID NO 3, SEQ ID NO 4, SEQ ID NO 5, SEQ ID NO 6 or SEQ ID NO 7.

18. A kit comprising an isolated nucleic acid molecule consisting of the sequence of SEQ ID NO 3, SEQ ID NO 4, SEQ ID NO 5, SEQ ID NO 6, SEQ ID NO 7, or the complement of SEQ ID NO 3, SEQ ID NO 4, SEQ ID NO 5 SEQ ID NO 6 or SEQ ID NO 7.

* * * * *